(12) United States Patent
Nielsen et al.

(10) Patent No.: US 6,180,566 B1
(45) Date of Patent: *Jan. 30, 2001

(54) HERBICIDE PREPARATION, A PROCESS FOR PRODUCING IT AND AN ACTIVATING ADDITIVE FOR APPLICATION THEREWITH

(75) Inventors: Erik Nielsen, Greve; Arne Oxbøl, Rødovre, both of (DK)

(73) Assignee: KVK Agro A/S, Koge (DK)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/031,730

(22) Filed: Feb. 27, 1998

Related U.S. Application Data

(63) Continuation of application No. 08/464,863, filed as application No. PCT/DK94/00094 on Mar. 8, 1994, now Pat. No. 5,795,847.

(30) Foreign Application Priority Data

Mar. 9, 1993 (DK) .................................... 0255/93
Oct. 5, 1993 (DK) .................................... 1117/93

(51) Int. Cl.$^7$ ............................. A01N 25/30; A01N 57/02
(52) U.S. Cl. ............................. 504/206; 504/363
(58) Field of Search .................... 504/206, 363

(56) References Cited

U.S. PATENT DOCUMENTS

| | | | |
|---|---|---|---|
| 5,258,358 | 11/1993 | Kocur et al. ................. | 504/205 |
| 5,258,359 | 11/1993 | Kassebaum et al. ........ | 504/206 |
| 5,356,861 | 10/1994 | Gednalski et al. .......... | 504/206 |

FOREIGN PATENT DOCUMENTS

| | | |
|---|---|---|
| 3926800A1 | 2/1991 | (DE) . |
| 2348/88 | 9/1988 | (DK) . |
| 0243872 | 11/1987 | (EP) . |
| 0388239 | 9/1990 | (EP) . |
| 0441764A1 | 8/1991 | (EP) . |
| 0448538A1 | 9/1991 | (EP) . |
| 0498145A1 | 8/1992 | (EP) . |
| 0498785A1 | 8/1992 | (EP) . |
| 2033569 | 3/1993 | (ES) . |
| 2661315 | 10/1991 | (FR) . |
| 2 230 955 | 11/1990 | (GB) . |
| 2233229 | 1/1991 | (GB) . |
| 2245170 | 1/1992 | (GB) . |
| 200076 | 1/1988 | (HU) . |
| WO92/12637 | 8/1992 | (WO) . |
| WO92/21686 | 12/1992 | (WO) . |

OTHER PUBLICATIONS

STN International, Chemical Abstracts, vol. 119, No. 9, "Herbicidal glyphosate salt concentrate", Aug. 30, 1993.

*Primary Examiner*—S. Mark Clardy
(74) *Attorney, Agent, or Firm*—Jackson, Price, Holman & Stern, PLLC

(57) ABSTRACT

Stable, concentrated herbicide preparation comprising at least one herbicide with at least one amino group, at least one carboxylic acid group and at least one phosphor containing acid group suspended in finegrained form in a liquid phase, and at least 5% a by weight of a dissolved electrolyte; a process for producing said herbicide preparation and an activating additive (adjuvant) for combination with said herbicide preparation. Preferred suspensions comprise the herbicides glyphosate and glufosinate and the electrolyte ammonium sulphate, acting synergistically. It has not hitherto been possible to incorporate high concentrations of synergistic electrolytes in liquid concentrates of said herbicides.

25 Claims, No Drawings

HERBICIDE PREPARATION, A PROCESS FOR PRODUCING IT AND AN ACTIVATING ADDITIVE FOR APPLICATION THEREWITH

This is a continuation of application Ser. No. 08/464,863 filed Sep. 8, 1995 now U.S. Pat. No. 5,795,847, which is a national stage of PCT/DK94/00094, filed Mar. 8, 1994.

The present invention relates to concentrated herbicide preparations comprising at least one herbicide being fine-grained and suspended in an aqueous electrolyte solution, said herbicide comprising at least one primary, secondary or tertiary amino group and at least one carboxylic acid group and at least one phosphor containing acid group, a process for producing it and an activating, concentrated additive for application in combination with said herbicides.

It is customary to produce herbicide preparations as suspensions in water. But normally the content of electrolytes in the aqueous phase is low, since a high content of electrolytes in water has a tendency to lower the solubility of the additives being necessary to stabilize the herbicide suspension. Amongst these additives, the surfactants are particularly important, said surfactants being necessary to ensure the wetting in connection with the grinding of the suspended herbicide, and being often desirable in connection with the intrusion of the herbicides in the weeds. Often only a few surfactants are suitable to ensure, in an appropriately broad temperature interval from −10° C. to approximately 50° C., that the suspension is effectively wetted and also flows satisfactorily. Additionally the suspensions almost always contain soluble, viscosity regulating compounds, ensuring that the viscosity in a broad temperature interval does not fall below a certain low value in order to avoid precipitation of the suspended herbicide. A too high content of electrolytes in the aqueous phase might lead to the gelatination or precipitation of the viscosity regulating compounds. The surfactants as well as the viscosity regulating compounds and eventually a certain amount of a dissolved glycol component can ensure, that the suspension after freezing and subsequent unfreezing thaws out again as a flowable, not gritty suspension.

In published european patent application EP 388.239 A1 pesticide suspensions are described, in which a certain amount of electrolytes is desirable. The suspension of finely ground pesticides in a concentration from 10–70% by weight in aqueous, structured systems of surfactants is described. The following pesticides are mentioned explicitly: ethofumesate, phenmedipham, dazomet, mancozeb, methylene bisthiocyanate, amitraz and triforine. None of these pesticides contains both an acid and an amino group. The wording "structured systems of surfactants" is intended to mean aqueous systems, in which the surfactants form mesophases comprising structures larger than conventional spherical micelles and mutually interacting to form thixotropy in the aqueous medium. The structure comprises multilayers of spherulites or lamellae dispersed or emulsified as rods or discs in an outer aqueous phase, the size being normally 0.5–20 $\mu$m. In the 14 examples of the application the not surface active electrolytes are present in an amount of 1.2–6.4% by weight of the total composition. It is a characteristic feature of this system, that the surfactant and the electrolyte must be adapted to each other as regards composition and amount to obtain the desired, stable structure.

Hungarian patent HU 200076 discloses, how the sedimentation tendency of aqueous suspensions may be avoided by addition of electrolytes to the suspensions. According to the patent lumps of surfactant will be formed when an electrolyte is added, causing the liquid to be turbid as the stabilisation takes place. It is not clearly evident from the patent whether the stabilisation is caused by crystallisation of surfactant on the surface of the suspended pesticide or by crystallisation of surfactant as a new phase (compare EP 388.239), or by the viscoelasticity caused by the precipitation. The improved stability is evaluated by centrifugation through indication of the not sedimented part. Only one of the samples (table 7) is subjected to normal long term storage. The preferred electrolyte is diammonium hydrogen phosphate. According to the patent 5–10% diammonium hydrogen phosphate provides optimal effect. It is not surprising that addition of electrolyte increases the stability of an aqueous suspension, the viscosity normally being increased and frequently causing the suspension to gelatinate. It is contrarily surprising, that the patent does not indicate the viscosity of the evaluated suspensions. All the examples comprise glycol, frequently about 10%. This addition counteracts the salting-out caused by the electrolyte.

The adjustment of the viscosity of a suspension by changing an eventual content of electrolyte, surfactant and glycol being well-known, this technic, however, is almost never practiced at the final adjustment of viscosity, because the effect is very dependent of temperature and difficult to reproduce. Centrifugal tests are notoriously of no relevance for the long term stability of suspensions. HU 200076 does not disclose that the amount of emulsifier necessary for sufficient wetting of the suspended pesticide may be reduced when an electrolyte is added. Similarly it is not disclosed in HU 200076, that the surfactant or the viscosity regulating polysaccharide may be omitted following the addition of an electrolyte. There is a certain overlap between the intervals of added electrolyte in HU 200076 and in the present invention, but the optimal amount of electrolyte in the present invention is above the most effective in HU 200076. The described pesticides are atrazine, isoproturon, bensultap, fluomethuron, lindane, thiophanat-methyl and elementary sulfur. None of these pesticides comprises a carboxylic acid group or a phosphor containing acid group.

It is well known that ammonium sulphate acts synergistically on the biological effect of glyphosate and glufosinate. For instance the patent literature contains many examples of combinations of glyphosate and ammonium sulphate, and in practice the farmer usually adds supplementary ammonium sulphate when diluting the glyphosate for use.

Danish patent application no. 2348/88 describe liquid, aqueous solutions of glyphosate with ethoxylated monoamines as surfactants. The possibility of dissolving additional ammonium sulphate exists, but this will lead to a lowering of the dissolvable quantity of glyphosate. Therefore, the maximum amount of glyphosate in a solution containing 280 g/l ammonium sulphate is approximately 120 g/l.

UK patent application GB 2.233.229 A describes a similar system, the ethoxylated monoamines being replaced by ethoxylated diamines. The typical, aqueous solutions contain 200 g/l ammonium sulphate and 75 g/l of glyphosate as its isopropylammonium salt.

UK patent application GB 2.245.170 A claims solutions of glyphosate containing ethoxylated phosphate esters as surfactants. In the examples, where ammonium sulphate has been added supplementary to the formulation in amounts of 200–300 g/l, the glyphosate constitutes 75 g/l corresponding to 100 g/l of the isopropylammonium salt.

In European patent application EP 441.764 A1 is mentioned, that alkoxylated, quaternary ammonium compounds especially coethoxylated-propoxylated quaternary ammonium compounds, is environmentally more acceptable and less skin and eye irritating than ethoxylated fatty amines. It is stated, that aqueous solutions of glyphosate in combinations with said surfactants also can contain ammonium sulphate, but no examples with such formulations are given. On the other hand two solid compositions containing ammonium sulphate are described.

In European patent application EP 498.785 A1 glyphosate formulations are mentioned, which contain esters of sorbitol and fatty acids as surfactants in combination with another surfactant. It is mentioned, that these formulations whether aqueous solutions or solid, finely distributed formulations may also contain ammonium sulphate or other inorganic ammonium salts. The system, however, seems to be best suited for solid formulations.

European patent application EP 498.145 A1 describes solid compositions containing glyphosate as free acid or salt, an inorganic ammonium salt (preferably ammonium sulphate) and alkyl-glycoside or alkylpolyglycoside as surfactant.

European patent application EP 448.538 A1 describes combinations of glyphosate and oxyfluorfen in solid formulations, additionally containing ammonium sulphate and other inorganic compounds.

International patent application WO 92/12637 deals with solid, preferably extruded or granulated formulations containing glyphosate in combination with alkaline compounds. A reaction takes place between the glyphosate and the alkaline compound either during the production process or during the subsequent mixing with the diluent water to totally or partly neutralize the glyphosate as salt whereby it dissolves easier and more quickly. The formulations shown besides comprise surfactants and frequently ammonium sulphate.

In danish patent application no. 6490/89 solid formulations of glyphosate in acid form containing a saturated $C_{16-18}$-fatty alcohol, being ethoxylated with approximately 25 moles ethyleneoxide are described. The formulations may additionally contain supplementary ammonium sulphate.

In german Offenlegungsschrift DE 3.926.800 A1 water-dispersable granulates are mentioned, containing a herbicide (anyhow preferably glufosinate) and 10–90% by weight of various anionic wetting agents. Examples of formulations with various amounts of ammonium sulphate are shown.

European patent application 243.872 A1 discloses pesticide preparations, comprising inter alia glyphosate dispersed in an oil containing, liquid phase. The addition to the formulations of ammonium sulphate is not mentioned.

French patent application 2.661.315 discloses the suspension of glyphosate and derivatives thereof in an organic solvent. The organic solvent might be water miscible, and it is mentioned that up to 50% of the solvent may be replaced by water. Furthermore the composition may comprise ammonium sulphate, which is characterized as an adjuvant. The form of the ammonium sulphate of the composition is not apparent from the description, but in the 5 examples of the application, the ammonium sulphate together with the glyphosate compound seems to be totally suspended or dissolved only to a limited extent in the liquid phase.

International patent application WO 92/21686 describes the production of trimethylsulfonium salt of glyphosate for instance by the reaction of glyphosate trimethylsulfonium hydrogen sulphate with an alkaline compound like ammonia. The application does not mention herbicidal suspensions in relation to the present invention. No description is found, neither in the patent description nor in the examples, of significant amounts of glyphosate being at any time suspended in an electrolyte solution and certainly not in a stable form. The principles of the present invention for formulating glyphosate, seem never to have been considered.

Many of the examples shown demonstrate the desirability of combining the herbicides glyphosate or glufosinate with ammonium sulphate and selected surfactants in one and the same formulation. Advantageously the formulation is as concentrated as possible.

As far as liquid, dissolved formulations are concerned, the ammonium sulphate has a salting-out effect on the dissolved salts of glyphosate and glufosinate, as well as on the dissolved surfactants, and an upper limit exists of the concentration of the solution dependent on the actual surfactant. Environmental requirements on the detergents, for instance as to biodegradability, poor toxicity towards fishes and low skin and eye irritation may reduce still further the number of relevant wetting agents. Besides, the various surfactants differ significantly in their promotion of the biological effect of glyphosate and glufosinate.

Therefore, the trend in recent developments is towards solid, finely dispersed and non-dusty formulations. Although the solubility of ammonium sulphate in water is big, the speed of dissolution of ordinary, commercial, crystalline ammonium sulphate in water in practice is hardly acceptable. Consequently, the crystalline ammonium sulphate frequently needs to be grinded before being mixed with glyphosate or glufosinate or preferably a salt thereof, the selected surfactant(s) and additive(s) being subsequently added. Amongst the additives adhesives, absorbing fillers or anticaking agents should be mentioned, which are necessary to obtain a finely dispersed, non-caking and easily flowing, solid formulation of adequate storage stability. For these processes an expensive formulation equipment is necessary.

Despite the availability of these new types of highly sofisticated solid formulations, for example micro granulates or finely extruded materials, many users prefer to have liquid formulations. One of the reasons is the easier measuring-out of how much of the composition to use, when the formulation is a liquid one.

Besides suppliers of spraying equipment are developing new types of equipment, in which the automatic mixing with the diluent water takes place immediately before spraying, said method being advantageous of several reasons. For instance, all the farmer has to do is to fill the water tank with water and place the concentrated pesticide preparation in the spraying equipment, the desired dilution automatically being made when driving. In such spraying systems the dosage of liquid formulations will be easier than that of solid formulations.

SUMMARY OF THE INVENTION

The present invention is based on the surprising fact, that a stable suspension can be attained by grinding a powdered herbicide with at least one amino group, at least one carboxylic acid group and at least one phosphor containing acid group in a bead mill in a higly concentrated solution of an electrolyte, which is not a surfactant per se, even if no surfactant is present.

In order to explain in greater detail the reasons for the above fact being surprising, a number of requirements normally to be met when producing a stable suspension concentrate of a herbicide in a liquid phase—a so-called "flowable"—are listed below.

1) The herbicide must be very poorly soluble in the actual liquid, for instance water, because when soluble to a certain extent in the liquid, the dissolved part of the herbicide, by cooling of the liquid, will precipitate, mainly on the biggest of the fine, solid particles present in the preparation, leading to crystal growth. When reheated mainly the smallest crystals of herbicide will dissolve and so on. At constantly fluctuating temperatures, which is normally the case in practice, this means a continuous crystal growth and an increased sedimentation tendency. This will normally give rise to serious storage problems.

2) It is necessary to add a surfactant to ensure optimal wetting of the suspended particles of herbicide in the liquid. If the wetting is unsufficient, the suspension will become thick and consequently impossible to grind in wet condition in a bead mill.

3) It is necessary to add a viscosity regulating agent in order to stabilize the final two-phased preparation.

4) It is necessary to add dissolved additives, which ensure that the product after drastic cooling and possibly freezing again thaws into a stable and homogenous form without forming gritty lumps. This can be obtained by adding electrostatically acting dispersion agents, polymers (acting sterically hindering) and glycol compounds (lowering the freezing point of the liquid). Frequently a combination of these additives is used.

DETAILS

Herbicides with at least one primary, secondary and/or tertiary amino group, at least one carboxylic acid group and at least one phosphor containing acid group normally have a relatively high solubility in water: about 0.1 corresponding to 1000 ppm or more, preferably at least 0.4% corresponding to 4000 ppm; by way of example the solubility of glyphosate is approximately 1% by weight in pure water at 20° C.

By addition of an electrolyte during suspension in an aqueous phase crystal growth of suspended herbicide is prevented, in fact a salting out of the herbicide takes place. However, as mentioned above, a high content of electrolyte prevents the usual addition of additives mentioned under items 2, 3 and 4 above, apart from the freezing point lowering glycol compounds, said additives being normally regarded as absolutely necessary for forming stable herbicide suspensions.

According to the invention, the wet grinding of a compound, which is almost insoluble in the liquid phase, seems to take place without serious viscosity problems, even if no surfactant is added. This is very untypical. The reason could be, that the herbicide molecule contains an amino group as well as two acid groups. This explanation is made probable by the fact, that the surfactants being most difficult to salt out in electrolyte solutions, are those containing both negatively and positively charged hydrophilic groups.

The fact, that the grinding can take place without viscosity problems, even when no surfactant is added, is probably an essential condition for realising the invention. Even if a surfactant were added, the salting out from the electrolyte of the compound would generally be so extensive, that the wetting effect of the insignificant amount still dissolved in the water phase would be too small to influence significantly on the grinding. The surfactant, however, is still desirable. As mentioned above said surfactant is necessary to ensure the optimum, biological effect of the formulation, and it might contribute to the stabilization of the final formulation, i.e. ensure that the formulation remains homogenous and does not separate. Apparently the finely grinded suspended herbicide and the added, finely distributed surfactant mutually interact to produce a mixture of an advantageous pseudoplastic or thixotropic character. Accordingly, it is possible to produce stable formulations comprising as the sole components water with dissolved electrolyte, suspended glyphosate and surfactant. It is even possible to produce stable suspensions using no surfactants at all.

When a surfactant is included in the suspension the surfactant mainly appears to be uniformly distributed on the finely grinded herbicide particles. This fact might contribute further to the stabilization of compositions, inter alia the coating causes the density differences between the suspended and the liquid phase to be reduced.

There is some overlap regarding type of formulation and possible components between the present invention and French patent application 2.661.315. It is therefore relevant to explain the differences between the two systems.

In the French application the liquid phase mainly comprises an organic solvent, while the present invention particularly uses water, which economically and usually environmentally is the most advantageous solvent. But that difference is not the decisive one. The fact that the electrolyte according to the present invention is not suspended in the liquid phase, but normally totally dissolved in it, is far more important. It leads to the following advantages:

a) The grinding of the ammonium sulphate is avoided (it is difficult to describe this advantage, but the ammonium sulphate is so hard and difficult to grind, and these difficulties can really only be understood through practical experience in the laboratory). After all it seems correct to conclude, that even if the ammonium sulphate is pre-grinded in dry condition, the final grinding on the bead mill gives rise to great problems regarding material tear, low production speed and risk of production stop.

b) An adjustment of the density of the grinded herbicide and the density of the electrolyte solution in order to minimize the difference is possible, whereby the separation tendency in the suspension becomes very low. By coating the surfactant on the suspended herbicide further variations can be obtained. In French application 2.661.315, the herbicide as well as the electrolyte has to be suspended in the liquid phase, and there is accordingly no such possibility of adjusting the density of the liquid phase or of coating the suspended particles with the surfactants.

c) By dissolving the electrolyte in a liquid phase a desirable lowering of the solubility of the suspended herbicide is obtained. Hereby a greater long term stability is obtained, because the risk of crystal growth is reduced (a generally accepted fact regarding suspension preparations).

d) In suspension preparations the amount of suspended solid material in a liquid phase must be below a certain upper limit. Normally the practical limit is about 500 g/l suspension. In glyphosate preparations containing ammonium sulphate the desired content of ammonium sulphate as well as that of glyphosate is high, and this is not possible to obtain if both compounds are to be suspended. When the ammonium sulphate is dissolved in the water phase and the glyphosate only is dispersed herein, it is possible to increase the amounts of ammonium sulphate as well as glyphosate.

Consequently the present invention differs from the description and the 5 examples in French application 2.661.315 by having at least 5% by weight of electrolyte dissolved in the liquid, continuous phase. Example 5 of the present application shows differences between the two systems and clarifies the advantages of having the electrolyte dissolved in the liquid phase.

The herbicide preparations being stable means, that the suspended herbicide in concentrated form does not precipitate or separate into solid lumps, which on shaking of the preparation in the commercial packing can not be resuspended in the liquid. Moreover the herbicide preparations must be able to stand storage in the commercial packing for at least 12 year under normal storage conditions. The preparations being on concentrated form means, that the product is in a commercial packing and that a dilution must take place before use.

The invention accordingly relates to stable, concentrated herbicide preparations comprising at least one herbicide in an amount of 5–58% by weight, said herbicide being fine-grained and suspended in a liquid aqueous phase, and said herbicide containing at least one primary, secondary or tertiary amino group, at least one carboxylic acid group and at least one phosphor containing acid group, said herbicide preparations being characterized by comprising at least 5% by weight of an electrolyte, which is dissolved in the liquid, aqueous phase and, which is not a surfactant.

If nothing else is stated, the indication "% by weight" or "%" in the present application means % by weight of the total composition.

For economical reasons it is advantageous, that the suspensions are as concentrated as possible. On the other hand the solubility properties of the electrolytes determines the minimum of the water content. The lower limit for the water content is low, because a part of the water theoretically can be substituted by an organic, water miscible solvent, which is also able to dissolve the electrolyte. In the preferred suspensions of the invention, the water content is max. 65%, preferably max. 60%, especially max. 55%, particularly max. 50% and specially max. 45%, compare claim 2; in the suspensions the water content is generally min. 12%, preferably min. 15%, especially min. 20%, particularly min. 25% and specially min. 30%, i.e. intervals of for instance 12–65%, preferably 15–60%, especially 20–55%, particularly 25–50% and specially 30–45%.

The liquid, aqueous phase should be continuous regarding water, but can contain water miscible, organic solvents. The amount of water in the continuous solvent phase will normally constitute at least 52%, preferably at least 55%, especially at least 60%, particularly at least 67% and specially at least 75% calculated as % by weight of the total amount of solvent in the liquid and continuous, aqueous phase (compare claim 3). (Water is calculated as solvent).

Said suspended herbicides with at least one amino group, at least one carboxylic acid group and at least one phosphor containing acid group will frequently be such, where the phosphor containing acid group is selected from amongst phosphonic acids and phosphinic acids.

Specially preferred herbicides are glyphosate (N-(phosphonomethyl)-glycine), glufosinate (4-(hydroxy(methyl)phosphinoyl)-DL-homoalanine), bilanafos (4-hydroxy(methyl)phosphinoyl)-L-homoalanyl-L-alanyl-L-alanin) and/or glyphosine (N,N-bis(p-hosphionomethyl)glycine), compare claim 4.

The actual suspended herbicides of the invention are applicable as such, i.e. in their free, non-neutralized form, or they can be reacted with acid or base into completely or partly neutralized salts, compare claim 5. Amongst the acidic salts, hydrochlorides and sulfuric acid salts should be mentioned. Salts formed by reaction with base are for instance alkanolamine salts, amine salts, sodium salts and potassium salts and especially ammonium salts. Amongst the more special salts, trimethylsulfonium and trimethylsulfoxonium salts should be mentioned.

Preferably the suspended herbicide is present in its free, non-neutralized form or as a mixture of a salt and free, non-neutralized form comprising max. 80%, preferably max. 70%, especially max. 60% and specially max. 50% of the herbicide transformed into a salt or, as a third possibility, comprising min. 50%, preferably min. 60%, especially min. 70% and specially min. 80% of the herbicide transformed into a salt like an ammonium salt or a metal salt (by "%" is meant mole percents). Since the herbicide contains two or more acid groups, the transformation into salt is to be calculated for the most acidic acid group only, the other groups being not included in the calculation.

Specially preferred suspensions are those, in which the herbicides are in their free, non-neutralized form or completely or partly reacted with ammonia into the respective ammonium salts, compare claim 6.

The amount of the suspended herbicide in the compositions of the invention is preferably min. 10%, especially min. 14%, particularly min. 18% and specially min. 21%; on the other hand the suspended herbicide constitutes max. 51%, especially max. 44%, particularly max. 38% and specially max. 33% so, i.e. intervals of for instance preferably 10–51%, especially 14–44%, particularly 18–38% and specially 21–33%, compare claim 7.

The described herbicide suspensions are generally characterized by the fact that said herbicides, when dissolved in water (1 part concentrate to 99 parts of water, eventually to 499 parts of water) dissolves completely in the diluent water. The pH in a 1% solution in water is min. 1, preferably min. 1.5, especially min. 2 and specially min. 2.5. The pH will normally be max. 7, preferably max. 6, especially max. 5 and specially max. 4.4 so, i.e. intervals of pH of for instance 1–7, preferably 1.5–6, especially 2–5 and specially 2.5–4.4.

If desired, different herbicides in combination can be used in the herbicide suspensions of the invention.

The invention also relates to stable, activating additives (adjuvants) on concentrated form, said adjuvants being active when admixed with glyphosate- and/or glufosinate preparations for combatting weeds, and said additives comprising at least one surfactant in an amount of 4–58% by weight, said surfactant being emulsified, suspended and/or dissolved in a liquid, aqueous phase; the composition of the adjuvant being further characterized by comprising at least one undissolved, fine-grained, not biologically active viscosity regulating filler acting to prevent separation of the surfactant, said viscosity regulating filler comprised in an amount of min. 0.3% by weight, and said liquid, aqueous phase being characterized by comprising an electrolyte, which is dissolved in the liquid, aqueous phase and, which is not a surfactant, in an amount of min. 5%, compare claim 19.

Such a stable, activating additive is in a way an intermediate Lor the production of a concentrated suspension of glyphosate and/or glufosinate according to the invention, since the herbicide suspension can be produced from the additive simply by admixing finely grinded herbicide.

To produce the herbicidal solution/suspension for use, the farmer may make use of the additive, too. He just has to mix it with a glyphosate- or a glufosinate preparation. The form of the herbicide is of minor importance in this connection, for instance a finely grinded powder, a solid granulate, a solution in an appropriate solvent or even a suspension may be used.

The wording "electrolyte", whether used in connection with the herbicide preparations or the additive according to the invention, is intended to mean a single salt or a single salt or a mixture of two or more salts. Generally the electrolyte per se can not be regarded as a herbicide.

The electropositively charged part of the electrolyte can be as well organic as inorganic, and the electronegatively charged part can be as well organic as inorganic, but normally a salt is preferred, in which either the positively charged or the negatively charged part is inorganic; a completely inorganic electrolyte is especially advantageous, compare claim 8.

Among the electrolytes with characteristic, electropositively charged ions amine salts, alkanol amine salts, trimethylsulfonium salts, trimethylsulfoxonium salts and metal salts with mono-, di- or trivalent metal ions should be mentioned. Specially preferred electrolytes are selected from among ammonium salts, compare claim 9.

Among the electrolytes with characteristic, electronegatively charged ions carboxylic acid salts, di- and tricarboxylic acid salts, hydroxycarboxylic acid salts, sulfonic acid salts and phosphonic acid salts should be mentioned. Specially preferred electrolytes are selected from among sulphates, chlorides, phosphates, phosphites, nitrates, nitrites, rhodanides, sulfamates, sulfites, dithionites and thiosulphates, compare claim 10.

Partly acidic salts such as ammonium hydrogensulphate and ammonium dihydrogenphosphite formed from not monovalent acid rests can be used as well.

As specially preferred electrolytes ammonium sulphate, ammonium chloride, ammonium hydrogenphosphate, ammonium nitrate, ammonium rhodanide, ammonium sulfamate and ammonium thiosulphate should be mentioned.

The amount of the dissolved electrolyte in the composition is preferably min. 10%, more preferably min. 12,5%, especially min. 15%, particularly min. 18% and specially min. 21%. On the other hand the amount of the dissolved electrolyte is generally max. 60%, preferably max. 53%, more preferably max. 49%, especially max. 46%, particularly max. 41% and specially max. 36% so, i.e. intervals of for instance 5–60%, preferably 10–53%, more preferably 12,5–49%, especially 15–46%, particularly 18–41% and specially 21–36%, compare claim 11.

Furthermore the composition may comprise limited amounts of undissolved electrolyte. But usually this undissolved electrolyte will be undesirable, because of stability and succeeding solubility problems. A content of undissolved electrolyte might result from a separation at low temperatures.

Under certain special conditions, however, it is desirable for the composition to comprise undissolved electrolyte (salt). This will be the case, if the undissolved salt is coated and therefore can not dissolve before the composition is mixed with water before the spraying in the field. Under such conditions crystal growth of the salt is prevented, and the extra content of coated and dispersed salt can enhance the biological effect of the preparation.

The total amount of electrolyte in the composition is preferably at least 18%, especially at least 21%, particularly at least 23% and specially at least 25%.

The solubility of the selected electrolyte in water influences the maximum amount of the electrolyte in the composition. So the upper limit for the amount of the electrolyte is generally max. 75%, preferably max. 68%, especially max. 60%, particularly max. 54% and specially max. 48% by weight of the electrolyte solution.

Preferred herbicidal compositions are such, in which the selected herbicide is glyphosate or glufosinate, and the selected electrolyte is ammonium sulphate.

To ensure the optimum biological effect, as mentioned above, said herbicide suspensions preferably also comprise at least one surfactant constituting 1–50%, said surfactant being emulsified, suspended and/or eventually dissolved in the liquid, aqueous electrolyte solution. The amount of the surfactants in the composition is preferably min. 3%, particularly min. 6% and specially min. 10%; on the other hand the amount of the surfactants preferably is max. 38%, especially max. 31% and specially max. 26i, i.e. intervals of for instance preferably 3–38%, especially 6–31% and specially 10–26%, compare claim 12.

Regarding the adjuvant according to the invention the amount of the surfactants in the composition is preferably min. 7%, particularly min. 11% and specially min. 14%; on the other hand the amount of the surfactants preferably is max. 48%, particularly max. 40% and specially max. 35%, i.e. intervals of for instance preferably 7–48%, particularly 10–40% and specially 14–35%.

The wording "surfactants" includes emulsifiers, as well as dispersing and wetting agents. A surfactant might be a polymer with a molecular weight of below approximately 15,000 Dalton with many hydrocarbyl- and/or hydrocarbylene groups, or it must always contain at least one hydrocarbyl- or hydrocarbylene group containing at least 8 carbon atoms, or a polymethylesiloxane with at least 8 silicium atoms. Besides the surfactant must contain at least one hydrophilic group, for example a polyoxyethylene group, an amine group, a sulfonic acid group or a phopsphate ester group, but this is no exhaustive characterization of a surfactant. Surfactants comprise compounds described in sales brochures relating to emulsifiers, dispersing and wetting agents and in catalogues and works of reference for such. As examples of works of reference McCutcheon's publications: "Detergent & Emulsifiers International Edition" and "North American Edition", Glen Rock, N.J. 07452, USA are to be mentioned.

In the present application, the following definitions apply: Hydrocarbyl (R—) designates a linear aliphatic or branched aliphatic alkyl-, alkenyl- or alkynylgroup, illustrated by ethyl ($-CH_2CH_3$), ethenyl ($-CH{=}CH_2$) or ethynyl ($-C{\equiv}CH$). Hydrocarbylene (—R—) designates a linear aliphatic or branched aliphatic alkylene, alkenylene- or alkynylene group, illustrated by ethylene ($-CH_2CH_2-$), ethenylene ($-CH{=}CH-$) or ethynylene ($-C{\equiv}C-$).

The surfactants may be of non-ionic, anionic, cationic or amphoteric nature. Amines or quaternary compounds being additionally ethoxylated, are always regarded as cationic in this description.

The herbicide suspension and the adjuvant according to the invention may comprise a mixture of different surfactants, for instance a mixture of two non-ionic surfactants or a mixture of a non-ionic and a ionic surfactant.

The non-ionic surfactants may be selected from among such which are ethoxylated, propoxylated or co-ethoxylated/propoxylated surfactants. The hydrophobic part of the non-ionic surfactants may be selected from the group consisting of mono-, di- or tristyrylphenol, naphtol, mono-, di- or tristyrylnaphtol, dicyclohexylphenol, mono-, di- or tristyryldicyclohexylphenol, phenylphenol, mono-, di- or tristyrylphenylphenol, benzylphenol, mono-, di- or tristyrylbenzylphenol, formaldehyde condensed phenol or formaldehyde condensed naphtol, in which the above mentioned hydrophobic parts may be substituted with one, two, three or four $C_{1-15}$-alkyl groups, or the hydrophobic part may be selected from mono-, di-, tri- or tetra-$C_{1-18}$-alkylphenol or mono-, di-, tri- or tetra-$C_{1-18}$-alkylnaphtol or $C_{8-30}$-hydrocarbylalcohol, $C_{8-30}$ hydrocarbylcarboxylic acid, $C_{8-30}$-hydrocarbylene-di-carboxylic acid and abeetinic acid (rosin acid). Other corresponding non-ionic surfactants being methylated in the terminal OH-group of the polyalkoxylene groups or in which said OH-group is linked to a new hydrocarbyl-group, preferably with the same composition as already mentioned, may be used, too.

From among the other types of non-ionic surfactants block-polymers (copolymerisates) of ethylene oxide and styren and of ethylene oxide (ethylene glycol) and propylene oxide (propylene glycol) should be mentioned, whose molecular weight is in the interval from 1000 to approximately 15,000 Dalton, preferably from 1500 to approximately 12,000 Dalton and specially from 1,800 to approximately 10,000 Dalton.

Other preferred non-ionic surfactants are the ethoxylated, propoxylated or co-ethoxylated/propoxylated vegetable oils as for example ricinus oil; fatty acid esters of polyalcohol as for example sorbitol, in itself an emulsifier, which can be alkoxylated further (ethoxylated, propoxylated or co-ethoxylated/propoxylated); monoglycerides, diglycerides and polyalcoholates of natural fatty acids, which can be esterified further with $C_{1-4}$-monocarboxylic acid (e.g. acetic acid), $C_{1-10}$-dicarboxylic acid (e.g. adipic acid) and $C_{1-6}$-hydroxycarboxylic acid (e.g. lactic acid), and which can be alkoxylated further. Among other non-ionic wetting agents of relevance N-$C_{4-16}$-alkylpyrrolidone, specially N-$C_{8-16}$-alkylpyrrolidone, hydrocarbylcarboxylic amide and alkoxylated variants hereof; alkoxylated hydrocarbylmercaptane, alkoxylated thiophenol and alkoxylated thionaphtol should be mentioned.

Specially preferred non-ionic surfactants are alkylglycosides, alkylpolyglycosides, alkoxylated alkylglycosides, alkoxylated alkylpolyglycosides, alkoxylated saccharides, alkoxylated polysaccharides, alkoxylated acetylene diols containing a symmetrically substituted triple bond and ethoxylated polymethylsiloxanes, compare claim 13.

The anionic surfactants may be selected from the groups comprising phosphate esters of for instance alkoxylated styrylphenols, alkylphenols and hydrocarbylalcohols; substituted and unsubstituted sulfonic acids; esters and halfesters of sulfosuccinic acid; monosulphate esters of $C_{8-20}$-hydrocarbylalcohol and styrylalcohol derivatives; naphtalene sulfonic acid derivatives; sulfonated vegetable oils and sulfonated mono- and diesters of natural fatty acids and sulfonated fatty acids; $C_{8-30}$-hydrocarbylcarboxylic acid; $C_{8-30}$-hydrocarbylene-dicarboxylic acids illustrated by $C_{4-16}$-alkylsubstituted succinic acid; polycarboxylic acids; taurides and sarkosides and sulfamido carbonic acids. Additional types of anionic surfactants are (the corresponding) derivatives of polymethylsiloxanes.

The cationic surfactants may be selected from the group comprising $C_{8-30}$-hydrocarbylamine and $C_{8-30}$-hydrocarbyl-di- and triamine being alkoxylated with min. 1 preferably min. 2, especially min. 5 and specially min. 8 oxyethylene and/or oxypropylene groups; quaternary amines with min. one $C_{8-30}$-hydrocarbyl and/or hydrocarbylene group and their alkoxylated derivatives; and amine modified polymethylsiloxanes.

The amphoteric surfactants are characterized by comprising at least one $C_{8-30}$-hydrocarbyl or at least one $C_{8-30}$-hydrocarbylene group and always at least one amino group and further one anionic group. The anionic group may preferably be selected from among carboxylic acid, sulfonic acid and phosphonic acid.

Surfactants with ionic groups may be used in their free, unreacted form, but will often be totally or partly reacted to salt. The composition should not at the same time comprise significant amounts of an anionic as well as a cationic surfactant, and the surfactants are generally selected accordingly.

Concerning those surfactants, for which it is possible to calculate a HLB-value (HLB=Hydrofil-Lipofil-Balance), this HLB-value should preferably not be too low. The HLB-value should be min. 3, preferably min. 4, especially min. 5, particularly min. 6 and specially min. 7.

Even though the presence of a surfactant in the herbicide suspension of the invention is desirable for biological reasons, a suspension comprising no surfactant has commercial interest, because of the possibility of adding separately the surfactant at the admixing stage of said suspension with the diluent water. The surfactant might be formulated as an activating additive according to the invention. The advantage of this system is, that the farmer may adjust individually the surfactant to the amount of herbicide.

It is possible to adjust the suspension to enable most surfactants to physically enter it. The suspended herbicide helps preventing the surfactant from separating out. The surfactant is generally present in the suspension in a non-structured form. Therefore in most of the described herbicide suspensions comprising a surfactant, the surfactant will separate as an independent, liquid phase or as solid particles in case the suspended herbicide and solid additives, if any, are removed from the suspensions.

The present invention does not relate to the final dilutions made at the user level. The invention relates to concentrates only, being herbicide preparations or activating additives, which according to the invention are formulated in a new and more advantageous way. Since dilutions of use, made from the concentrates to a certain extent are well known, because they can be obtained by separate addition of ammonium sulphate to known products, and they are known to posses a particularly satisfying biological effect, it seems redundant to proove the effect of the described compositions. There might be differences in the pH-values of the dilutions. For instance the pH-value of the herbicide preparations according to the invention is frequently low, because the glyphosate is preferably used in its non-neutralized form, but this fact is known to be of no biological importance. Reference is made in this connection to Danish patent application 6490/89, specially dealing with glyphosate on non-neutralized form.

In order to further stabilize the compositions physically to ensure the smallest extent possible of sedimentation of the herbicide during storage i.e. to ensure a minor extent only of separation of a clear liquid, it might be desirable for the suspensions to comprise a viscosity regulating compound. At low electrolyte concentration, the viscosity regulating compound might be a water soluble polymer being completely or partly dissolved (swelled) in the water phase. Among the possible types thereof polycarboxylates, polyvinylpyrrolidones and copolymerisates thereof should be mentioned. Another type of water soluble polymers is polysaccharides, such as xanthane gum.

The optimal content of electrolyte is normally so high, that watersoluble polymers, f.ex. xanthane gum (Kelzan S or Rohdopol B 23), if present in the suspension, would either gelatinate or separate on undissolved form.

According to claim 14 the compositions of the invention preferably comprise viscosity regulating compounds selected from among finely distributed fillers tending not to sediment in the electrolyte solution, and of a particle size of max. 5 μm, preferably max. 1 μm, especially max. 0.3 μm and specially max. 0.1 μm. The fillers might be naturally occurring and synthetic clays and silicates, for instance natural silicium dioxides such as diatomaceous earth; calcium- and magnesiumsilicates, such as talcs; magnesium aluminium silicates, such as attapulgites and vermiculites; aluminium silicates, such as kaolinites, montmorillonites and mica; synthetic, hydrated silicium oxide units and synthetic calcium or aluminium silicates; natural resins and synthetic resins such as coumarone resins, polyvinyl chloride and styrene polymers and copolymers; solid fertilizers such as superphosphates. Inorganic fillers are preferred. Especially preferred are fillers such as attapulgit, bentonite and hectorite and organic derivatives thereof such as Bentone™. In addition to the separation suppressing effect an added filler frequently improves the grinding of the pesticide, particularly if the grinding is performed in the wet state in a bead mill.

As regards herbicide suspensions of the invention the appropriate amount of the viscosity regulating filler generally is max. 18%, preferably max. 11%, especially max. 7% and specially max. 4%; on the other hand the amount of the viscosity regulating filler should be min. approximately 0.1%, preferably min. 0.3%, especially min. 0.5% and specially min. 0.9%, i.e. intervals of for instance 0.1–18%, preferably 0.3–11%, especially 0.5–7% and specially 0.9–4%, compare claim 15.

As regards the additive of the invention an appropiate amount of the viscosity regulating filler is max. 22%, preferably max. 18%, especially max. 14% and specially max. 10%; on the other hand the amount of the viscosity regulating filler should be min. 1%, especially min. 2% and specially min. 3.6%, i.e. intervals of for instance 0.3–22%, preferably 1–18%, especially 2–14% and specially 3.6–10%.

Whether a herbicide suspension or an activating additive of the invention, when this composition comprises a viscosity regulating, water soluble polymer, an appropriate amount thereof is 0.01–3%, preferably 0.03–2%, especially 0.1–1.5% and specially 0.3–1%.

Amongst other viscosity regulating compounds having the additional effect of improving the cold stability and acting hygroscopiccally, the compositions of the invention might comprise glycols, polyglycols, glycerine, polymerized glycerine, glycolethers, polyglycolethers, polyalcohols and urea, all having a solubility in water at 20° C. of at least 1% by weight. Examples of glycols are ethylene glycol, propylene glycol and hexylene glycol. Examples of polyglycols are diethylene glycol, triethylene glycol, polyethylene glycol, dipropylene glycol, tripropylene glycol and water soluble polypropylene glycols. Examples of polyglycolethers are diethylene glycol butylether, dipropylene glycol methylether, dipropylene glycol butylether and tripropylene glycol butylether. Examples of polyalcohols are sorbitol, trimethylolpropan and pentaerythritol. None of the polyglycols, glycolethers and polyalcohols should be surfactants. The components of the abovementioned group of compounds may be present in the composition in an amount of max. 25%, preferably max. 18%, especially max. 11% and specially max. 7%; on the other hand they should be present in an amount of approximately min. 0.1%, preferably min. 0.7%, especially min. 1.4% and specially min. 2.4%, i.e. intervals of 0.1–25%, preferably 0.7–18%, especially 1.4–11% and specially 2.4–7%.

The compositions of the invention might comprise hygroscopic compounds, possibly also acting to stabilize pH and selected from the group consisting of hydroxycarboxylic acids, di- and tricarboxylic acids and their hydroxy acids, said acids being present as free acids and having a solubility in water at 20° C. of at least 1% by weight. Examples of such acids are lactic acid, oxalic acid, succinic acid, tartaric and citric acid. The amount of these acids in the composition may be approximately 0.1–22%, preferably 0.4–16%, especially 1–11% and specially 2–7%.

Another group of compounds being able to promote the biological effect, for instance by improving the intrusion of the herbicides into the treated plants, is the group of oily compounds. The composition of the invention accordingly may comprise oils or oily compounds, the solubilities thereof in water at 20° C. being below 1% by weight, the boiling points thereof at atmospheric pressure being min. 200° C., preferably min. 230° C. and specially min. 260° C., and which are selected from the group comprising carbonhydride oils, triglyceride oils, preferably synthetic ester oils with one or two estergroups per molecule, hydrocarbylcarboxylic acids, hydroxyhydrocarbylcarboxylic acids, hydrocarbylalcohols, hydrocarbylenedialcohols, water insoluble polypropylene glycols and silicone oils. An example of a carbonhydride oil is mineral oil. Examples of triglyceride oils are vegetable oils and marine oils. Examples of carboxylic acids are oleic acid, lauric acid and pelargonic acid. An example of hydroxyhydrocarbylcarboxylic acid is ricinoleic acid. Examples of hydrocarbylalcohols are n-decanol and isodecanol.

The number of carbon atoms in the ester oils with one or two ester groups per molecule is 8–72, preferably 10–60, especially 12–46 and specially 14–44. Those ester oils which do not additionally comprise ether groups are preferred. Examples thereof are methyl oleate, butyl oleate, 2-ethylhexyl stearate, propylene glycol dioleate and di-(2-ethylhexyl) sebacate.

The components of this group of oils or oily compounds are present in the composition of the invention in an amount of max. 24%, preferably max. 17%, especially max. 11% and specially max. 7%; on the other hand they should be present in an amount of min. 0.1%, preferably min. 0.7%, especially min. 1.4% and specially min. 2.4%, i.e. intervals of for instance 0.1–2.4%, preferably 0.7–17%, especially 1.4–11% and specially 2.4–7%.

The herbicide suspension according to the invention is usually produced by a process, where the herbicide and eventually other components are grinded and admixed with the other components. The same principle applies for the production of the additive according to the invention. A subsequent adjustment may be necessary.

The grinding and possibly the admixing may preferably take place in a bead mill, compare claim 17, for instance at a temperature in the interval of 0–50° C. In order to maintain the temperature in this interval cooling of the bead mill with water or ice water will usually be necessary. If the surfactant has a higher melting point, it might be desirable to raise the temperature of the mill to 50–60° C. for a period. This may be effected by temporarily stopping the cooling water. The surfactant is added in the molten state at the higher temperature, and finely grinded filler, if any, is usually added before the cooling with cooling water is resumed.

To avoid foaming it is frequently advantageous to postpone the addition of surfactant to after the grinding.

The average particle size of the herbicide in the compositions of the invention, as for instance determined using a Malvern Particle Sizer of the type 3600 E using low effect laser light diffraction technic or an equivalent method, must be max. 72 $\mu$m, specifically max. 48 $\mu$m, preferably max. 29 $\mu$m, especially max. 19 $\mu$m, particularly max. 13 $\mu$m and specially max. 8 $\mu$m; on the other hand the average particle size must be min. 0.2 $\mu$m, specifically min. 0.3 $\mu$m, preferably min. 0.5 $\mu$m, especially min. 1 $\mu$m, particularly min. 2 $\mu$m and specially min. 3.5 $\mu$m, i.e. intervals of for instance 0.2–72 $\mu$m, specifically 0.3–48 $\mu$m, preferably 0.5–29 $\mu$m, especially 1–19 $\mu$m, particularly 2–13 $\mu$m and specially 3.5–8 $\mu$m, compare claim 16.

The invention also relates to a special process for producing the herbicide suspension according to the invention, said process being characterized by comprising the following steps, compare claim 18: Firstly a highly concentrated solution of the herbicide as salt in water is formed. To this solution either acid or base is added to precipitate the herbicide in completely or partly free non-salt form; the electrolyte solution is formed from the rest of the salt initially having formed salt with the herbicide, and the added amount of acid or base, and the precipitation is controlled so as to produce particles of a sufficiently small size to reduce or preferably leave out the subsequent grinding on the bead mill. In order for the herbicide particles to become of a sufficiently small size, the addition of acid or base preferably takes place as controlled as possible, which normally means, that the addition takes place during simultaneous cooling and/or vigorous stirring and/or through a suitable injector system.

Specially preferred herbicide suspensions comprise glyphosate suspended in ammonium sulphate, said suspensions being produced by adding sulfuric acid to solutions of the ammonium salt of glyphosate or adding ammonia to a solution of the sulfuric acid salt of glyphosate, preferably while cooling and continuously stirring.

Or the suspensions may be produced by wet grinding (on a bead-mill) of the herbicide in the electrolyte solution. Other additives may be added either before or after the grinding.

The viscosity of preferred compositions of the invention at 25° C. is max. 7900 cp (mPa×s), preferably max. 4900 cP, especially max. 2900 cP and specially max. 2000 cP. On the other hand the viscosity should be min. 70 cP, preferably min. 150 cP, especially min. 275 cP and specially min. 440 cP, i.e. intervals of for instance 70–7900 cP, preferably 150–4900 cP, especially 275–2900 cP and specially 440–2000 cP, as measured with a Brookfield viscosimeter equipped with a spindel of the type RV.

As packaging material for the suspensions, certain polymers may be used, which are soluble in water and insoluble in the electrolyte solutions, in which the herbicide is suspended. Among such polymers polyvinylalcohol and methyl cellulose should be mentioned.

In the preferred dilutions of use of the herbicide preparations and the activating additives, the amount of the concentrate in the final dilution of use is 0.2–10%, preferably 0.4–6%, especially 0.7–4% and specially 1–3% by weight of the dilution of use, corresponding to a dosage per hectar of 0.3–15 l/ha, preferably 0.6–9 l/ha, especially 1–6 l/ha and specially 1.5–4.5 l/ha.

The amount of the herbicide, for instance glyphosate or glufosinate, constitutes 0.2–4 kg/ha, preferably 0.3–3 kg/ha, especially 0.5–2.2 kg/ha and specially 0.8–1.5 kg/ha, calculated on an active ingredient basis.

The examples below illustrate the production of stable suspensions according to the invention.

EXAMPLE 1

Experiments 1–5 (see table A) demonstrates the suspension of glyphosate in free, non-neutralized form in an aqueous solution of ammonium sulphate. Calculated on the aqueous solution the amount of ammonium sulphate is 40% in all 5 experiments corresponding to a saturation in water at approximately 0° C. In all of the examples, ethoxylated fatty amines are used as surfactants.

For the manufacture of the compositions 1 and 2 the Genamine (the ethoxylated fatty amine) was initially dissolved in a part of the water, following which the pH was adjusted with concentrated sulfuric acid to pH=3.5. The rest of the water was then added and subsequently the ammonium sulphate was stirred in, leading to the precipitation of the chief of the Genamine. The mixture was transferred as quantitatively as possible to a mini-mill with a volume of maximally 50 ml from the company Eiger Engineering Ltd., Warrington, Cheshire, England, being filled with 1–2 mm zirkonium oxide pearls. The mill was started immediately at its highest speed, and the addition of glyphosate was started. After 5 minuttes all glyphosate was added. The grinding was continued for further approximately 10 minuttes. Attagel was added, and the grinding was continued for maximally 5 minuttes.

For the manufacture of the compositions 3, 4 and 5, the ammonium sulphate was initially dissolved in the total amount of water, following which the concentrated sulfuric acid was added, and the solution was transferred to the mini-mill. The mill was started at its highest speed, following which the addition of glyphosate was started. After 5 minuttes all glyphosate was added. The grinding was continued for further approximately 10 minuttes. Genamin was added immediately followed by Attagel, and the grinding was continued for approximately 5 minutes.

In table A, the various components and the amounts thereof are listed.

Samples of the above compositions were stored in 100 ml glass bottles with screw caps for 1 to approximately 4 weeks before the beginning of the accelerated testing. It was initially evaluated, whether the sample had separated a clear aqueous phase, and whether the surfactant had separated out on its own. The results of all evaluations are listed in table A. Subsequently the sample was shaken. The viscosity was visually evaluated, and the average particle size of the grinded glyphosate particles was estimated microscopically at 256×. (It is very difficult to use a particle sizer for so many samples, because the samples must be measured in concentrated salt solutions possibly further saturated with glyphosate, in order to ensure, that the samples are not dissolved in the water. It is also important that the concentrated salt solution does not contain undissolved impurities, which might disturb the measurements). It was also estimated, whether the added surfactants had separated out as oily drops If so, the estimated size of the drops was noted. If no oily drops could be observed, a "n.d." (not detected) is stated in the table. It should be noted, that any microscopic airbubbles present may give rise to a false positive result.

After the evaluation a part of the content of the 100 ml bottles was transferred to 60 ml glass bottles to fill all bottles approximately half. The 60 ml bottles were stored for 14 days at 55° C. The 100 ml bottles were stored as follows:

72 hours: 55° C.
24 hours: Ambient temperature
24 hours: −18° C.
24 hours: Ambient temperature
96 hours: 55° C.
24 hours: Ambient temperature
24 hours: −18° C.
24 hours: Ambient temperature
24 hours: 55° C.
Totally 14 times 24 hours.

After this testing period both groups of samples were cooled to ambient temperature and evaluated as mentioned above. Supplementary the speed of dissolution was determined as follows: 1 ml suspension was pipetted off and placed in a 150 ml beaker containing 100 ml deionized water. The mixture was stirred on a magnetic stirrer of moderate speed using a 4 cm magnet so as to produce an approximately 1 cm deep vortex in the diluent water, and the period of time until no more undissolved glyphosate could be observed was measured in seconds. All observations are listed in table A.

Evaluation and conclusion.

The results of the evaluation are estimated subjectively. The value indicated, however, may constitute a sufficient basis for estimating whether the suspensions during storage undergo undesirable changes of a stability destroying nature.

The most difficult evaluation is that of the viscosity. It is evaluated, whether the samples show pseudoplastic properties, but the presence of such properties can not be estimated visually for all samples. The pseudoplastic properties, being desirable in suspension preparations in order to avoid sticking sediments, are therefore only indicated for those samples, in which they are unmistakable. In the tables the following definitions are used:

| | | |
|---|---|---|
| Sufficiently | = | sufficiently flowing, i.e. and appropriate viscosity. |
| Easily | = | easily flowing. The sample has an appropriately low viscosity, but sedimentation might take place during long time storage. |
| Very easily | = | very easily flowing. Probably a too low viscosity, but no sticking sedimentation was observed. |
| Slightly viscous | = | the viscosity is not very far removed from the upper limit of what is acceptable, and it should not be increased. |
| Somewhat viscous | = | unacceptable, high viscosity. |
| Viscous | = | much too high viscosity. |
| Pseudoplastic | = | an appropriate viscosity of the desired pseudoplastic nature. |
| Clearly pseudoplastic | = | pseudoplastic, perhaps too viscous when the sample is at rest. |
| Upp. cl. phase | = | upper clear phase |

All samples in table A shows acceptable storage properties. Some uncertainty exists as to the results of the measurements of the speeds of dissolution, but the level must be characterized as satisfactory.

TABLE A

| | Experiment no. | | | | |
|---|---|---|---|---|---|
| | 1 | 2 | 3 | 4 | 5 |
| Components | Composition in % | | | | |
| Deionized water | 41.6 | 41.1 | 41.0 | 41.0 | 40.8 |
| Ammonium sulphate | 27.8 | 27.4 | 27.4 | 27.4 | 27.2 |
| Glyphosate, 98% | 20.8 | 20.6 | 20.6 | 20.6 | 20.4 |
| Genamin T 150 (1) | 6.9 | 6.8 | | | |
| Genamin O 80 (2) | | | 6.8 | | |
| Genamin C 100 (3) | | | | 6.8 | |
| Genamin C 020 (4) | | | | | 6.8 |
| Sulfuric acid, 98% | app. 1.5 | app. 1.4 | 2.1 | 2.1 | 2.7 |
| Attagel (5) | 1.4 | 2.7 | 2.1 | 2.1 | 2.1 |
| Total weight (g) | 144 | 146 | 146 | 146 | 147 |
| Density (g/ml) | 1.30 | 1.29 | 1.28 | 1.28 | 1.25 |

TABLE A-continued

| | Experiment no. | | | | |
|---|---|---|---|---|---|
| | 1 | 2 | 3 | 4 | 5 |
| Glyphosate (g/l) | 270 | 266 | 264 | 264 | 255 |
| Ammonium sulphate (g/l) | 361 | 353 | 351 | 351 | 340 |
| Evaluation before storage | | | | | |
| Appearance | 15% upp. cl. phase | 10% upp. cl. phase | 10% upp. cl. phase | 10% upp. cl. phase | 10% upp. cl. phase |
| Viscosity | pseudo-plastic | slightly viscous | slightly viscous | pseudo-plastic | pseudo-plastic |
| Particle size ($\mu$m) | app. 10 | app. 10 | 5–10 | app. 10 | 5–10 |
| Oil drops ($\mu$m) | n.d. | n.d. | n.d. | n.d. | n.d. |
| Evaluation after storage at various temperatures | | | | | |
| Appearance | 30% upp. cl. phase | 20% upp. cl. phase | 15% upp. cl. phase | 25% upp. cl. phase | 25% upp. cl. phase |
| Viscosity | easily | sufficiently | sufficiently | easily | easily |
| Particle size ($\mu$m) | app. 10 | 10–15 | app. 10 | 10–15 | 5–10 |
| Oil drops ($\mu$m) | n.d | n.d. | n.d. | n.d. | n.d. |
| Speed of dissol. (s) | 4 | 6 | 3 | 3 | 2 |
| Evaluation after storage 14 days at 55° C. | | | | | |
| Appearance | 15% upp. cl. phase | 5% upp. cl. phase | 10% upp. cl. phase | 10% inner cl. phase | 15% upp. cl. phase |
| Viscosity | pseudo-plastic | slightly viscous | pseudo-plastic | pseudo-plastic | pseudo-plastic |
| Particle size ($\mu$m) | app. 10 | 10–15 | app. 10 | 10–15 | app. 10 |
| Oil drops ($\mu$m) | n.d. | n.d. | n.d. | n.d. | n.d. |
| Speed of dissol. (s) | 3 | 4 | 4 | 2 | 7 |

EXAMPLE 2

Experiments 6–10, 11–15, 16–20, 21–25 and 26–29 in the tables B, C, D, E, and F describe glyphosate compositions comprising various surfactants in varying amounts. The ratio glyphosate/surfactant is about 2/1 corresponding to the usual ratio in most commercial products. The amount of finely distributed fillers varies from 0 to 2% by weight. In all of the experiments the amount of the electrolyte ammonium sulphate is varying from app. 20 to 27% by weight. The grinding is performed in a mini-mill as described for the samples 3–5 in table A, the sulfuric acid addition, however, being omitted.

The melting points of Marlipal 1618/25 and Radiasurf 7417 are about 55° C. Therefore, the mixtures in experiments 26 and 27 were heated to 50–55° C. during the addition of Marlipal and Radiasurf.

Evaluation and conclusion:

No tendency to separate sticking sediments was observed in any of the examples. After shaking the flowing properties seem acceptable. A subsequent re-evaluation of the experiments revealed that air bubbles by mistake under the microscope had been regarded as oil drops. No separate oil layers were seen. The speeds of dissolution in water are generally very good.

No relevant comparison with other suspension preparations can be made, because of the aqueous suspension preparations, dissolving in the diluent water, being an unusual type of formulation.

TABLE B

| | Experiment no. | | | | |
|---|---|---|---|---|---|
| | 6 | 7 | 8 | 9 | 10 |
| Component | Composition in % | | | | |
| Deionized water | 40.5 | 40.5 | 40.5 | 40.5 | 40.5 |
| Ammonium sulphate | 27.0 | 27.0 | 27.0 | 27.0 | 27.0 |
| Glyphosate, 98% | 20.3 | 20.3 | 20.3 | 20.3 | 20.3 |
| Ethoquad C/25 (6) | 10.2 | | | | |
| Emcol CC 55 (7) | | 10.2 | | | |
| Ampholyt SKKP-70 (8) | | | 10.2 | | |
| Synperonic NP-10 (9) | | | | 10.2 | |
| Tween 20 (10) | | | | | 10.2 |
| Attagel (5) | 2.0 | 2.0 | 2.0 | 2.0 | 2.0 |
| Total weight (g) | 148 | 148 | 148 | 148 | 148 |
| Density (g/ml) | 1.28 | 1.27 | 1.27 | 1.27 | 1.27 |
| Glyphosate (g/l) | 260 | 258 | 258 | 258 | 258 |
| Ammonium sulphate (g/l) | 346 | 343 | 343 | 343 | 343 |
| Evaluation before storage | | | | | |
| Appearance | no separation | no separation | 15% lower cl. phase | 15% lower cl. phase | 10% lower cl. phase |
| Viscosity | slightly viscous | easily | slightly viscous | slightly viscous | slightly viscous |
| Particle size (μm) | app. 10 | app. 10 | 10–15 | 10–15 | 10 |
| Oil drops (μm) | n.d. | n.d. | n.d. | n.d. | 25–100 |
| Evaluation after storage at various temperatures | | | | | |
| Appearance | 20% upp. cl. phase | 30% upp. cl. phase | no separation | 20% upp. cl. phase | 15% upp. cl. phase |
| Viscosity | easily | easily | passende viscous | passende viscous | passende viscous |
| Particle size (μm) | app. 5 | app. 10 | app. 10 | app. 10 | 10–15 |
| Oil drops (μm) | n.d | n.d. | n.d. | n.d. | n.d. |
| Speed of dissol. (s) | 2 | 2 | 3 | 3 | 2 |
| Evaluation after storage 14 days at 55° C. | | | | | |
| Appearance | 10% upp. cl. phase | 25% upp. cl. phase | no separation | no separation | 10% upp. cl. phase |
| Viscosity | pseudo-plastic | easily | pseudo-plastic | slightly viscous | pseudo-plastic |
| Particle size (μm) | 5–10 | 5–10 | ap. 10 | 10–15 | 10–15 |
| Oil drops (μm) | n.d. | n.d. | n.d. | n.d. | n.d. |
| Speed of dissol. (s) | 4 | 1 | 3 | 7 | 2 |

TABLE C

| | Experiment no. | | | | |
|---|---|---|---|---|---|
| | 11 | 12 | 13 | 14 | 15 |
| Component | Composition in % | | | | |
| Deionized water | 40.5 | 40.5 | 40.5 | 40.5 | 40.5 |
| Ammonium sulphate | 27.0 | 27.0 | 27.0 | 27.0 | 27.0 |
| Glyphosate, 98% | 20.3 | 20.3 | 20.3 | 20.3 | 20.3 |
| Plantaren 225 (11) | 10.2 | | | | |
| Plantaren 600 CS (12) | | 10.2 | | | |
| Berol 02 (13) | | | 10.2 | | |
| Berol 922 (14) | | | | 10.2 | |
| Pleuriol PE6400 (15) | | | | | 10.2 |
| Attagel (5) | 2.0 | 2.0 | 2.0 | 2.0 | 2.0 |
| Total weight (g) | 148 | 148 | 148 | 148 | 148 |
| Density (g/ml) | 1.28 | 1.28 | 1.28 | 1.27 | 1.28 |
| Glyphosate (g/l) | 260 | 260 | 260 | 258 | 260 |
| Amm. sulphate (g/l) | 346 | 346 | 346 | 343 | 346 |
| Evaluation before storage | | | | | |
| Appearance | foaming 10% lower cl. phase | 15% lower cl. phase | no separation | no separation | 15% upp. cl. phase |
| Viscosity | pseudo-plastic | sufficiently | clearly pseudo-plastic | pseudo-plastic | pseudo-plastic |
| Particle size (μm) | 10–15 | app. 10 | app. 10 | app. 15 | app. 15 |
| Oil drops (μm) | n.d. | n.d. | <25 | 25–100 | >100 |
| Evaluation after storage at various temperatures | | | | | |
| Appearance | 5% inner cl. phase | 20% upp. cl. phase | 10% upp. cl. phase | 15% upp. cl. phase | 30% upp. cl. phase |
| Viscosity | sufficiently | sufficiently | sufficiently | easily | easily |
| Particle size (μm) | 10–15 | 10–15 | 5–10 | app. 15 | app. 15 |
| Oil drops (μm) | n.d | n.d. | n.d. | n.d. | n.d. |
| Speed of dissol. (s) | 46 | 12 | 2 | 6 | 2 |
| Evaluation after storage 14 days at 55° C. | | | | | |
| Appearance | no separation | 20% upp. cl. phase | no separation | no separation | no separation |
| Viscosity | pseudo-plastic | sufficiently | viscous* | pseudo-plastic | pseudo-plastic |
| Particle size (μm) | 10–15 | 10–15 | 5–10 | app. 15 | app. 15 |
| Oil drops (μm) | n.d. | n.d. | n.d. | n.d. | n.d. |
| Speed of dissol. (s) | 25 | 14 | 23 | 6 | 4 |

*screw cap leaky, crystals from the liquid observed.

TABLE D

| | Experiment no. | | | | |
|---|---|---|---|---|---|
| | 16 | 17 | 18 | 19 | 20 |
| Component | Composition in % | | | | |
| Deionized water | 40.5 | 40.8 | 40.8 | 40.5 | 40.5 |
| Ammonium | 27.0 | 27.2 | 27.2 | 27.0 | 27.0 |

TABLE D-continued

| | Experiment no. | | | | |
|---|---|---|---|---|---|
| | 16 | 17 | 18 | 19 | 20 |
| sulphate | | | | | |
| Glyphosate, 98% | 20.3 | 20.4 | 20.4 | 20.3 | 20.3 |
| Ethoquad C/25 (6) | | 10.2 | | | |
| Arkopon T hockonc. (17) | | | 10.2 | | |
| Berol 987 (18) | | | | 10.2 | |
| Surfadon LP 300 (19) | | | | | 10.2 |
| Aerosil R 972 (20) | | 1.4 | | | |
| Attagel (5) | 2.0 | | 1.4 | 2.0 | 2.0 |
| Total weight (g) | 148 | 147 | 147 | 148 | 148 |
| Density (g/ml) | 1.26 | 1.26 | 1.28 | 1.27 | 1.26 |
| Glyphosate (g/l) | 256 | 257 | 261 | 258 | 256 |
| Amm. sulphate (g/l) | 340 | 343 | 348 | 343 | 340 |
| Evaluation before storage | | | | | |
| Appearance | no separation | no separation | 10% lower cl. phase | no separation | no separation |
| Viscosity | slightly viscous | pseudo-plastic | pseudo-plastic | pseudo-plastic | pseudo-plastic |
| Particle size (μm) | app. 10 | 10–15 | app. 10 | app. 10 | app. 10 |
| Oil drops (μm) | n.d. | n.d. | n.d. | <25 | n.d. |
| Speed of dissol. (s) | 25–100 | 25–100 | n.d. | 25–100 | <25 |
| Evaluation after storage at various temperatures | | | | | |
| Appearance | 10% upp. cl. phase | 30% upp. cl. phase | 15% lower cl. phase | no separation | no separation |
| Viscosity | sufficiently | pseudo-plastic | pseudo-plastic | pseudo-plastic | pseudo-plastic |
| Particle size (μm) | 5–10 | app. 10 | app. 10 | app. 10 | app. 10 |
| Oil drops (μm) | n.d | n.d. | n.d. | <25 | n.d. |
| Speed of dissol. (s) | 3 | 3 | 14 | 2 | 13 |
| Evaluation after storage 14 days at 55° C. | | | | | |
| Appearance | no separation | 10% upp. cl. phase | no separation | no separation | no separation |
| Viscosity | slightly viscous | pseudo-plastic | slightly viscous | pseudo-plastic | some viscous |
| Particle size (μm) | 5–10 | 10–15 | 5–10 | 10–15 | 5–10 |
| Oil drops (μm) | n.d. | n.d. | n.d. | 25–100 | n.d. |
| Speed of dissol. (s) | 5 | 2 | 19 | 4 | 20 |

TABLE E

| | Experiment no. | | | | |
|---|---|---|---|---|---|
| | 21 | 22 | 23 | 24 | 25 |
| Component | Composition in % | | | | |
| Deionized water | 40.5 | 41.4 | 40.0 | 38.7 | 38.2 |
| Ammonium sulphate | 27.0 | 27.6 | 26.7 | 25.8 | 25.5 |
| Glyphosate, 98% | 20.3 | 20.7 | 20.0 | 19.4 | 19.1 |
| Berol OX 45-11 (21) | 10.2 | 10.3 | 13.3 | 16.1 | 15.9 |
| Attagel (5) | 2.0 | | | | 1.3 |
| Total weight (g) | 148 | 145 | 150 | 155 | 157 |
| Density (g/ml) | 1.26 | 1.26 | 1.26 | 1.25 | 1.25 |
| Glyphosate (g/l) | 256 | 261 | 252 | 243 | 239 |
| Ammonium sulphate (g/l) | 340 | 348 | 337 | 323 | 319 |
| Evaluation before storage | | | | | |
| Appearance | no separation | 15% lower cl. phase | 15% lower cl. phase | 15% lower cl. phase | 10% lower cl. phase |
| Viscosity | pseudo-plastic | easily | easily | easily | slightly viscous |
| Particle size (μm) | app. 15 | 10–15 | app. 15 | 10–15 | app. 10 |
| Oil drops (μm) | <25 | 25–100 | <25 | 25–100 | 25–100 |
| Evaluation after storage at various temperatures | | | | | |
| Appearance | 5% upp. cl. phase | 35% upp. cl. phase | 30% inner cl. phase | 20% lower cl. phase | 5% inner cl. phase |
| Viscosity | clearly pseudo-plastic | very easily | easily | sufficiently | pseudo-plastic |
| Particle size (μm) | 10–15 | 10–15 | 10–15 | 10–15 | app. 10 |
| Oil drops (μm) | <25 | n.d. | n.d. | n.d. | n.d. |
| Speed of dissol. (s) | 3 | 2 | 2 | 2 | 3 |
| Evaluation after storage 14 days at 55° C. | | | | | |
| Appearance | no separation | 30% upp. cl. phase | 15% inner cl. phase | 15% lower cl. phase | 10% lower cl. phase |
| Viscosity | clearly pseudo-plastic | very easily | easily | sufficiently | pseudo-plastic |
| Particle size (μm) | 10–15 | 10–15 | app. 15 | 10–15 | 10–15 |
| Oil drops (μm) | <25 | n.d. | 25–100 | n.d. | 25–100 |
| Speed of dissol. (s) | 10 | 1 | 1 | 2 | 3 |

TABLE F

| Experiment no | 26 | 27 | 28 | 29 | 30 |
|---|---|---|---|---|---|
| Component | Composition in % | | | | |
| Deionized water | 40.8 | 40.5 | 40.9 | 47.2 | 40.5 |
| Ammonium sulphate | 27.2 | 27.0 | 27.3 | 20.3 | 27.0 |
| Glyphosate, 98% | 20.4 | 20.3 | 20.5 | 20.3 | 20.3 |
| Marlipal 1618/25 (22) | 10.2 | | | | |
| Radiasurf 7417 (23) | | 10.2 | | | |
| Berol OX 45-11 (21) | | | 10.3 | 10.2 | |
| Berol 533 (24) | | | | | 10.2 |
| Aerosil R 972 (20) | | | 1.0 | | |
| Attagel (5) | 1.4 | 2.0 | | 2.0 | 2.1 |
| Total weight (g) | 147 | 148 | 146.5 | 148 | 148 |
| Density (g/ml) | 1.27 | 1.28 | 1.26 | 1.22 | 1.26 |
| Glyphosate (g/l) | 345 | 346 | 258 | 248 | 256 |
| Ammonium sulphate (g/l) | 259 | 260 | 344 | 248 | 340 |
| Evaluation before storage | | | | | |
| Appearance | no separation | no separation | no separation | no separation | no separation |
| Viscosity | slightly viscous | slightly viscous | pseudo-plastic | pseudo-plastic | pseudo-plastic |
| Particle size (μm) | app. 15 | app. 15 | app. 10 | app. 15 | app. 15 |
| Oil drops (μm) | n.d. | 25–100 | 25–100 | 25–100 | <25 |
| Evaluation after storage at various temperatures | | | | | |
| Appearance | 10% upp. cl. phase | 15% upp. cl. phase | 30% upp. cl. phase | 30% upp. cl. phase | 15% upp. cl. phase |
| Viscosity | clearly pseudo-plastic | pseudo-plastic | pseudo-plastic | pseudo-plastic | sufficiently |
| Particle size (μm) | 10–15 | app. 10 | app. 10 | 10–15 | app. 10 |
| Oil drops (μm) | n.d. | n.d. | 25–100 | n.d. | n.d. |
| Speed of dissol. (s) | 2 | 2 | 2 | 2 | 3 |
| Evaluation after storage 14 days at 55° C. | | | | | |
| Appearance | no separation | no separation | no separation | 20% upp. cl. phase easily | no separation |
| Viscosity | slightly viscous | pseudo-plastic | pseudo-plastic | | viscous* |
| Particle size (μm) | 10–15 | app. 10 | app. 10 | app. 15 | app. 10 |
| Oil drops (μm) | n.d. | n.d. | n.d. | n.d. | n.d. |
| Speed of dissol. (s) | 7 | 3 | 2 | 2 | 17 |

*Screw cap leaky, crystals from the liquid observed.

EXAMPLE 3

Experiments 31–35, 36–40, 41–45 and 46–49 in the tables G, H, I and J relate to various glyphosate compositions. Experiments 31–33 (table G) relate to compositions with ammonium salts different from ammonium sulphate. Experiments 34 and 35 (table G) relates to compositions comprising herbicide only suspended in an electrolyte solution. Experiments 36–40 (table H) show the use of potassium thiocyanate, sodium bromide and ammonium acetate as electrolyte. In the experiments 36 and 37, one of the acid groups in glyphosate is transformed into the sodium salt. In experiment 38, a little amount only of glyphosate is transformed into the sodium salt. In experiments 39 and 40, one of the acid groups in glyphosate is transformed into its ammonium salt. The experiments 41–45 (table I) relate to compositions comprising viscosity regulating, hygroscopic compounds. These are glycerine, propylene glycol, polyethylene glycol and lactic acid. Obviously the addition of these to the aqueous phase caused no tendency to separation of undissolved electrolyte. Experiments 46 and 47 relate to compositions further comprising oil. Experiment 48 and 49 relate to compositions comprising herbicide suspended in an electrolyte solution and small amounts of a viscosity regulating filler, but no surfactant.

The grinding is performed in a mini-mill as described above for the samples 3–5 in table A, the sulfuric acid addition being omitted.

In experiment 40 the composition comprising Marlipal 1618/25 was temporarily heated.

Evaluation and conclusion.

After shaking, the flowing properties seem satisfactory. The speeds of dissolution of the samples of experiments 34 and 35 comprising no surfactant, are inferior to those of the other samples, but acceptable anyhow. Generally speaking the speeds of dissolution are very good.

In the experiments 46 and 47, the oils apparently do not disperse onto the grinded glyphosate, unlike the surfactants. This conclusion is based partly on the microscopy and partly on the experiment 46, in which the sample, which had been stored at varying temperatures, at the end of the experiment had separated two upper, clear phases. This was not observed in experiment 47. In both samples, the oil was uniformly re-distributed in the compositions after shaking.

All samples from these experiments are at least acceptable.

TABLE G

| | Experiment no. | | | | |
|---|---|---|---|---|---|
| | 31 | 32 | 33 | 34 | 35 |
| Component | Composition in % | | | | |
| Deionized water | 27.4 | 34.0 | 40.5 | 36.9 | 33.1 |
| Ammonium sulfamate | 41.1 | 17.0 | | | |
| Ammonium sulphate | | 17.0 | | 24.6 | 22.1 |
| Ammonium nitrate | | | 27.0 | | |
| Glyphosate, 98% | 20.5 | 20.4 | 20.3 | 38.5 | 44.8 |
| Berol OX 45-11 (21) | 10.3 | 10.2 | 10.2 | | |
| Attagel (5) | 0.7 | 1.4 | 2.0 | | |
| Total weight (g) | 146 | 147 | 148 | 130 | 145 |
| Density (g/ml) | 1.35 | 1.29 | 1.25 | 1.33 | 1.38 |
| Glyphosate (g/l) | 277 | 263 | 254 | 512 | 618 |
| Electrolyte (g/l) | 555 | 439 | 338 | 327 | 305 |
| Evaluation before storage | | | | | |
| Appearance | 10% lower cl. phase | no separation | no separation | 20% upp. cl. phase | 10% upp. cl. phase |
| Viscosity | easily | slightly viscous | easily | passende viscous | slightly viscous |
| Particle size (µm) | app. 15 | 10–15 | 10–15 | 20–25 | app. 20 |
| Oil drops (µm) | 20–100 | 25–100 | 25–100 | n.d | n.d. |
| Evaluation after storage at various temperatures | | | | | |
| Appearance | 25% lower cl. phase | 10% upp. cl. phase | 30% upp. cl. phase | 30% upp. cl. phase | 20% upp. cl. phase |
| Viscosity | easily | pseudo-plastic | easily | passende viscous | slightly viscous |
| Particle size (µm) | app. 15 | 10–15 | 10–15 | 25–30 | app. 20 |
| Oil drops (µm) | <25 | n.d. | n.d. | n.d. | n.d. |
| Speed of dissol. (s) | 2 | 3 | 2 | 32 | 12 |
| Evaluation after storage 14 days at 55° C. | | | | | |
| Appearance | 15% lower cl. phase | no separation | 30% upp. cl. phase | 30% upp. cl. phase | 15% upp. cl. phase |
| Viscosity | easily | pseudo-plastic | easily | easily | slightly viscous |
| Particle size (µm) | app. 15 | 10–15 | app. 15 | app. 25 | app. 20 |
| Oil drops (µm) | n.d. | n.d. | 25–100 | n.d. | n.d. |
| Speed of dissol. (s) | 3 | 5 | 2 | 16 | 6 |

TABLE H

| | Experiment no. | | | | |
|---|---|---|---|---|---|
| | 36 | 37 | 38 | 39 | 40 |
| Component | Composition in % | | | | |
| Deionized water | 27.0 | 23.7 | 37.8 | 27.6 | 26.3 |
| Kalium thiocyanate | | 42.1 | | | |
| Ammonium sulphamate | 40.5 | | | | 39.5 |
| Natrium bromide | | | 29.7 | | |
| Ammonium acetate | | | | 33.8 | |
| Glyphosate, 98% | | | 20.3 | | |
| Glyphosate Na-salt | 20.3 | 23.0 | | | |
| Glyphosate NH₄-salt | | | | 27.6 | 23.0 |
| Berol OX 45-11 (21) | 10.2 | 9.9 | 10.1 | 9.2 | |
| Marlipal 1618/25 (22) | | | | | 9.9 |
| NaOH, 28% | | | 1.4 | | |
| Attagel (5) | 2.0 | 1.3 | 0.7 | 1.8 | 1.3 |
| Total weight (g) | 148 | 152 | 148 | 163 | 152 |
| Density (g/ml) | 1.33 | 1.24 | 1.39 | 1.35 | 1.35 |
| Glyphosate (g/l) | 270 | 285 | 282 | 373 | 310 |
| Electrolyte (g/l) | 539 | 522 | 413 | 456 | 533 |
| Evaluation before storage | | | | | |
| Appearance | 10% lower cl. phase | 5% lower cl. phase | 10% inner cl. phase | no separation | no separation |
| Viscosity | pseudo-plastic | sufficiently | easily | pseudo-plastic | clearly pseuplas. |
| Particle size (µm) | app. 15 | 10–15 | 10–15 | 30–50 | app. 15 |
| Oil drops (µm) | n.d. | <25 | n.d. | n.d. | 25–100 |
| Evaluation after storage at various temperatures | | | | | |
| Appearance | 10% lower cl. phase | 10% lower cl. phase | 25% upp. cl. phase | no separation | 10% lower cl. phase |
| Viscosity | easily pseuplas. | sufficiently | easily | clearly pseuplas. | clearly pseuplas. |
| Particle size (µm) | 20–25 | app. 15 | 10–15 | app. 50 | app. 20 |
| Oil drops (µm) | n.d | n.d. | n.d. | n.d. | n.d. |
| Speed of dissol. (s) | 3 | 5 | 3 | 9 | 2 |
| Evaluation after storage 14 days at 55° C. | | | | | |
| Appearance | 10% lower cl. phase | 10% lower cl. phase | 20% upp. cl. phase | no separation | no separation |
| Viscosity | clearly pseuplas. | sufficiently | easily | clearly pseuplas. | clearly pseuplas. |
| Particle size (µm) | 15–20 | 10–15 | app. 15 | 30–50 | app. 15 |
| Oil drops (µm) | n.d. | n.d. | n.d. | <25 | n.d. |
| Speed of dissol. (s) | 7 | 8 | 5 | 21 | 5 |

TABLE I

| | Experiment no. | | | | |
|---|---|---|---|---|---|
| | 41 | 42 | 43 | 44 | 45 |
| Component | Composition in % | | | | |
| Deionized water | 38.0 | 38.0 | 13.6 | 38.0 | 22.1 |
| Ammonium sulfamate | | | 20.5 | | 32.2 |
| Ammonium | 25.3 | 25.3 | | 25.3 | |

TABLE I-continued

| | Experiment no. | | | | |
|---|---|---|---|---|---|
| | 41 | 42 | 43 | 44 | 45 |
| sulphate | | | | | |
| Glyphosate, 98% | 19.0 | 19.0 | 20.6 | 19.0 | 25.0 |
| Berol OX 45-11 (21) | 9.5 | 9.5 | 10.3 | 9.5 | |
| Glycerin | 6.3 | | 34.3 | | |
| Propylene glycol | | | | | 20.7 |
| PEG E200 (27) | | 6.3 | | | |
| Lactic acid | | | | 6.3 | |
| Attagel (5) | 1.9 | 1.9 | 0.7 | 1.9 | |
| Total weight (g) | 158 | 158 | 146 | 158 | 140 |
| Density (g/ml) | 1.27 | 1.25 | 1.30 | 1.27 | 1.34 |
| Glyphosate (g/l) | 241 | 238 | 268 | 241 | 335 |
| Elektrolyt (g/l) | 321 | 316 | 267 | 321 | 431 |
| | Evaluation before storage | | | | |
| Appearance | no separation | no separation | no separation | no separation | 20% upp. cl. phase |
| Viscosity | pseudoplastic | pseudoplastic | pseudo plastic | clearly pseudoplastic | easily |
| Particle size (μm) | app. 15 | app. 10 | app. 15 | app. 15 | app. 10 |
| Oil drops (μm) | 25–100 | >100 | n.d. | 25–100 | n.d. |
| | Evaluation after storage at various temperatures | | | | |
| Appearance | no separation | 10% upp. cl. phase | 10% lower cl. phase | 5% upp. cl. phase | 35% upp. cl. phase |
| Viscosity | pseudoplastic | pseudoplastic | pseudoplastic | clearly pseudoplastic | easily |
| Particle size (μm) | 10–15 | app. 10 | app. 15 | app. 15 | app. 10 |
| Oil drops (μm) | n.d | n.d. | n.d. | n.d. | n.d. |
| Speed of dissol. (s) | 2 | 2 | 4 | 2 | 3 |
| | Evaluation after storage 14 days at 55° C. | | | | |
| Appearance | no separation | no separation | no separation | no separation | 25% upp. cl. phase |
| Viscosity | clearly pseudoplastic | pseudoplastic | pseudoplastic | clearly pseudoplastic | easily |
| Particle size (μm) | app. 15 | 5–10 | app. 15 | app. 15 | app. 10 |
| Oil drops (μm) | n.d. | n.d. | n.d. | n.d. | n.d. |
| Speed of dissol. (s) | 8 | 2 | 5 | 2 | 3 |

TABLE J

| | Experiment no. | | | |
|---|---|---|---|---|
| | 46 | 47 | 48 | 49 |
| Component | Composition in % | | | |
| Deionized water | 38.0 | 38.0 | 40.5 | 57.6 |
| Ammonium sulphate | 25.3 | 25.3 | 27.0 | 14.3 |
| Glyphosate, 98% | 19.0 | 19.0 | 30.5 | 25.2 |
| Berol 02 (13) | 6.3 | 6.3 | | |
| Hydropar 19 (25) | 9.5 | | | |
| Radia 7131 (26) | | 9.5 | | |

TABLE J-continued

| | Experiment no. | | | |
|---|---|---|---|---|
| | 46 | 47 | 48 | 49 |
| Attagel | 1.9 | 1.9 | 2.0 | 2.9 |
| Total weight (g) | 158 | 158 | 148 | 139 |
| Density (g/ml) | 1.22 | 1.21 | 1.34 | 1.22 |
| Glyphosate (g/l) | 232 | 230 | 409 | 174 |
| Ammonium sulphate (g/l) | 309 | 306 | 362 | 307 |
| | Evaluation before storage | | | |
| Appearance | 10% lower cl. phase | 15% lower cl. phase | no separation | 10% upp. cl. phase |
| Viscosity | sufficiently | sufficiently | pseudoplastic | easily |
| Particle size (μm) | app. 20 | app. 15 | 10–15 | 20–25 |
| Oil drops (μm) | >100 | 25–100 | n.d. | n.d. |
| | Evaluation after storage at various temperatures | | | |
| Appearance | 30% 2 upp. cl. phases | 30% lower cl. phase | 10% upp. cl. phase | 10% upp. cl. phase |
| Viscosity | sufficiently | pseudoplastic | pseudoplastic | easily |
| Particle size (μm) | app. 15 | 10–15 | 10–15 | 20–25 |
| Oil drops (μm) | >100 | >100 | n.d. | n.d. |
| Speed of dissol. (s) | 2 | 2 | 2 | 22 |
| | Evaluation after storage 14 days at 55° C. | | | |
| Appearance | 15% lower cl. phase | 20% lower cl. phase | no separation | no separation |
| Viscosity | sufficiently | pseudoplastic | pseudoplastic | easily |
| Particle size (μm) | app. 15 | app. 15 | 10–15 | 20–25 |
| Oil drops (μm) | >100 | >100 | n.d. | n.d. |
| Speed of dissol. (s) | 4 | 5 | 2 | 4 |

EXAMPLE 4

Experiments 50 and 51 in table K relate to compositions comprising no suspended herbicide, but a surfactant and a viscosity regulating filler suspended in an electrolyte solution.

Experiments 52–55 in table L relate to glufosinate suspended in an aqueous electrolyte solution. The electrolyte is either ammonium sulphate or ammonium sulfamate. The samples of experiments 52–54 further comprise a surfactant. The sample of experiment 55, on the other hand, comprises only water, ammonium sulphate and glufosinate.

The samples were produced in a mini-mill as described above.

Evaluation and conclusion.

Apparently, the glufosinate compositions are generally a little thin and therefore has a tendency to separate a clear liquid. This might be compensated for by changing the ratio between suspended solids and liquid electrolyte solution.

The speeds of distribution and dissolution are very favourable. The other physical properties appear completely satisfactory.

TABLE K

| | Experiment no. | |
|---|---|---|
| | 50 | 51 |
| Component | Composition in % | |
| Deionized water | 42.8 | 41.7 |
| Ammonium sulphate | 28.6 | 27.8 |

TABLE K-continued

|  | Experiment no. | |
| --- | --- | --- |
|  | 50 | 51 |
| Moussex 904 SE (28) |  | 0.7 |
| Ethoquad C/25 (6) | 25.0 |  |
| Berol OX 45-11 (21) |  | 27.8 |
| Attagel 40 (5) | 3.6 | 2.0 |
| Total weight (g) | 140 | 144 |
| Density (g/ml) | 1.15 | 1.14 |
| Glyphosate (g/l) | — | — |
| Ammonium sulphate (g/l) | 329 | 317 |
| Evaluation before storage | | |
| Appearance | 10% lower cl. phase | 10% lower cl. phase |
| Viscosity | sufficiently | sufficiently |
| Particle size (μm) | — | — |
| Oil drops (μm) | >100 | 25–100 |
| Evaluation after storage at various temperature | | |
| Appearance | 30% lower cl. phase | 25% lower cl. phase |
| Viscosity | sufficiently | sufficiently |
| Particle size (μm) | — | — |
| Oil drops (μm) | n.d. | n.d. |
| Evaluation after storage 14 days at 55° C. | | |
| Appearance | 10% lower cl. phase | 5% lower cl. phase |
| Viscosity | sufficiently | sufficiently |
| Particle size (μm) | — | — |
| Oil drops (μm) | n.d. | n.d. |

TABLE L

|  | Experiment no. | | | |
| --- | --- | --- | --- | --- |
|  | 52 | 53 | 54 | 55 |
| Component | Composition in % | | | |
| Deionized water | 41.0 | 27.2 | 42.9 | 40.0 |
| Ammonium sulphamate |  | 40.8 |  |  |
| Ammonium sulphate | 27.3 |  | 28.6 | 26.7 |
| Glufosinat, 97% | 20.5 | 20.4 | 21.4 | 33.3 |
| Berol OX 45-11 (21) | 10.2 | 10.2 |  |  |
| Arkopon T hochkonc (17) |  |  | 7.1 |  |
| Attagel | 1.0 | 1.4 |  |  |
| Total weight (g) | 146.5 | 147 | 140 | 120 |
| Density (g/ml) | 1.23 | 1.23 | 1.26 | 1.27 |
| Glufosinat (g/l) | 252 | 251 | 270 | 423 |
| Electrolyte (g/l) | 336 | 502 | 360 | 339 |
| Evaluation before storage | | | | |
| Appearance | 10% lower cl. phase | 20% lower cl. phase | 35% lower cl. phase | 30% lower cl. phase |
| Viscosity | sufficiently | easily | easily | easily |
| Particle size (μm) | 10–15 | app. 15 | app. 15 | 15–20 |
| Oil drops (μm) | n.d. | n.d. | >100 | n.d. |
| Evaluation after storage at various temperatures | | | | |
| Appearance | 15% lower cl. phase | 25% lower cl. phase | 45% upp. cl. phase | 30% inner cl. phase |
| Viscosity | easily | easily | easily | easily |
| Particle size (μm) | app. 10 | app. 10 | 10–15 | app. 15 |
| Oil drops (μm) | n.d. | n.d. | n.d. | n.d. |
| Speed of dissol. (s) | 4 | 6 | 3 | 18 |
| Evaluation after storage 14 days at 55° C. | | | | |
| Appearance | 15% lower cl. phase | 20% lower cl. phase | 45% upp. cl. phase | 30% inner cl. phase |

TABLE L-continued

|  | Experiment no. | | | |
| --- | --- | --- | --- | --- |
|  | 52 | 53 | 54 | 55 |
| Viscosity | sufficiently | easily | easily | easily |
| Particle size (μm) | 10–15 | 10–15 | app. 10 | 15–20 |
| Oil drops (μm) | n.d. | n.d. | n.d. | n.d. |
| Speed of dissol. (s) | 4 | 3 | 6 | 3 |

EXAMPLE 5

The purpose of the example is to illustrate the difference between the present invention and French application 2.661.315.

In the French application, the most hydrophilic solvent mixture and the mixture comprising the most water, is the mixture in example 1, comprising 250 g water and 300 g propylene glycol per liter. This mixture, therefore, is able to dissolve the most ammonium sulphate. 5% by weight of the weight of 1 liter product (1192 g) is 59.6 g. In experiment 56 (table M) this amount of ammonium sulphate is dissolved in the actual amount of water (250 g) followed by addition of the cited amount of propylene glycol (300 g) (both per liter product). A fast precipitation of ammonium sulphate is observed.

The actual surfactant of the French example 1, a derivative of an ethoxylated fatty amine, is not commercially available, and is synthesized from ethylene oxide (extremely poisonous). Experiments 57 and 58 are intended to show, that compounds being comparable to this surfactant do not solubilize the ammonium sulphate. Consequently the amount of dissolved ammonium sulphate in example 1 in FR 2.663.315 can not exceed 5% w/w. Genamin S 25 is the most ethoxylated of the commercially available ethoxylated fatty amines. In experiment 57 Genamin S 25 is admixed with propylene glycol, before the mixture is added to the ammonium sulphate solution. PEG 400 is polyethylene glycol comprising on an average 8 moles of ethylene glycol. Since this compound does not comprise any hydrophobic group, it is more hydrophilic than ethoxylated fatty amines, and therefore probably has a greater impact on the solubility of ammonium sulphate. In experiment 58 PEG 400 is admixed with the propylene glycol, before the mixture is added to the ammonium sulphaate solution. Both example 57 and 58 show a precipitation of ammonium sulphate following the addition of the propylene glycol mixtures to the aqueous ammonium sulphate solutions.

Conclusion.

None of the compositions in the examples of FR 2.661.315 comprises 5 w/w or more of dissolved ammonium sulphate.

TABLE M

| Experiment no. | 56 | 57 | 58 |
| --- | --- | --- | --- |
| Component | Composition in g | | |
| Deionized water | 250.0 | 250.0 | 250.0 |
| Ammonium sulphate | 59.6 | 59.6 | 59.6 |
| Propylene glycol | 300.0 | 300.0 | 300.0 |
| Genamin S 25 (29) |  | 200.0 |  |
| PEG 400 |  |  | 200.0 |
| Undissolved ammonium | Yes | Yes | Yes |

TABLE M-continued

| Experiment no. | 56 | 57 | 58 |
|---|---|---|---|
| sulphate at 25° C. | | | |

EXAMPLE 6

The product of experiment 59 in table N has been produced and grinded on a mini-mill in the same way as in experiments 6–30 in example 2.

The product of example 60 has been produced by initially dissolving the ammonium sulphate in water (40% ammonium sulphate solution) followed by admixture of propylene glycol, leading to a precipitation of ammonium sulphate. The stirring on the mini-mill was started, and the glyphosate was added in the usual way followed by admixture of Genapol OX-130.

The viscosity was measured at 20° C. by means of a Brookfield RVF-viscosimeter (gear 20). The much higher viscosity in experiment 60, comprising only half as much ammonium sulphate as experiment 59, is caused by the fact, that the ammonium sulphate in experiment 59 is totally dissolved in the liquid, aqueous phase, whereas the ammonium sulphate in experiment 60 is predominantly dispersed in the 50% w/w propylene glycol-/water phase.

At normal temperatures an ammonium sulphate solution comprises approximately 40% ammonium sulphate. In experiment 61 20 g ammonium sulphate was dissolved in the water phase followed by addition of propylene glycol, causing a precipitation of ammonium sulphate. Another 20 g ammonium sulphate was finely grinded in a blender with a view to adding it slowly during grinding before the addition of glyphosate, before the addition of Genapol and after the addition of Genapol, respectively.

In practice, the grinding showed up to be impossible, because the crystals of ammonium sulphate were too hard to grind and stopped the filter, keeping the pearls in the mill. Accordingly it was impossible to grind the ammonium sulphate in experiment 62, where no water was present to dissolve part of the ammonium sulphate.

Experiments 61 and 62 show, that ammonium sulphate precipitated as fine crystals from an aqueous solution by addition of a water-miscible, organic solvent gives rise to no problems, whereas finely grinded crystals of ammonium sulphate are difficult to grind further on a bead-mill.

TABLE N

| Experiment no. | 59 | 60 | 61 | 62 |
|---|---|---|---|---|
| Component | Composition in g | | | |
| Deionized water | 60.0 | 30.0 | 30.0 | |
| Ammonium sulphate | 40.0 | 20.0 | 40.0 | 40.0 |
| Propylene glycol | | 30.0 | 30.0 | 60.0 |
| Glyphosate, 98% | 30.0 | 30.0 | 30.0 | 30.0 |
| Genapol OX 130 (30) | 20.0 | 20.0 | 20.0 | 20.0 |
| Viscosity Brookfield at 20° C. | 1800 mPaxs | 3100 mPaxs | — | — |

EXAMPLE 7

A preferred composition of glyphosate in electrolyte solution comprises the following:
169.1 g glyphosate
225.4 g ammonium sulphate
338.2 g water
112.8 g Genapol OX-130 (30)

The above mentioned composition is produced as follows (using the method of claim 18):
169.1 g glyphosate is dissolved in 266 g water and 80 g aqueous 25% w/w ammonia solution together with 159,4 g ammonium sulphate in a beaker and is transferred to another container under vigorous stirring.

51.0 g sulfuric acid (969 w/w) is added over 10 minutes at approximately 25° C. 112.8 g molten Genapol OX-130 is added with vigorous stirring, the stirring being continued for 5 minutes.
End pH: 3.5
Density: 1.17 g/ml (the mixture contains some air)
1.25 g/ml (after evacuation)
Particle size: 20–25 μm

Chemicals

1. Genamin ™ T-150: Tallow fatty amine ethoxylated with 15 oxyethylene units (Hoechst).
2. Genamin ™ O-080: Oleylamine ethoxylated with 8 oxyethylene units (Hoechst).
3. Genamin ™ C-100: Fatty amine from coconut oil ethoxylated with 10 oxyethylene units (Hoechst).
4. Genamin ™ C-020: Fatty amine from coconut oil ethoxylated with 2 oxyethylene units (Hoechst).
5. Attagel ™ 40: Attapulgitclay, colloidal grades (Chemie-Mineralien GmbH).
6. Ethoquad ™ C25: (Coco)alkyl methylammonium chloride ethoxylated with 15 oxyethylene units (Akzo).
7. Emcol ™ CC 55: Alkoxylated quaternary ammonium salt (Witco).
8. Ampholyt SKKP-70: (Coco)alkyl-β-aminopropionic acid, 70% (Berol Nobel).
9. Synperonic ™ NP-10: Nonylphenol ethoxylated with 10 oxyethylene units (ICI).
10. Tween ™ 20: Sorbitanmonolaurate ethoxylated with 20 oxyethylene units (ICI).
11. Plantaren ™ 225: $C_{8-10}$-fatty alcohol glycoside, 70% (Henkel).
12. Plantaren ™ 600 CS UP: $C_{8-10}$-alkylpolyglycoside, 50% (Henkel).
13. Berol ™ 02: Nonylphenol ethoxylated with 6 oxyethylene units (Berol Nobel).
14. Berol ™ 922: Coethoxylated/-propoxylated alkylphenol (Berol Nobel).
15. Pleuriol ™ PE 6400: Copolymer of ethylene oxide (40%) and propylene oxide (60%) (BASF).
16. Tween ™ 85: Sorbitantrioleate ethoxylated with 20 oxyethylene units (ICI).
17. Arkopon ™ T hochkonc: Oleic acid methyltaurid, Na-salt 64% (Hoechst).
18. Berol ™ 987: Polyphenyl ether sulphate (Berol Nobel).
19. Surfadon ™ LP 300: N-alkylpryyolidon (GAF).
20. Aerosil ™ R 972: Synthetic silicic acid (Degussa).
21. Berol ™ OX 45-11: $C_{14-15}$-alkylalcohol ethoxylated with 11 oxyethylene units (Berol Nobel).
22. Marlipal ™ 1618/25: Stearylalcohol ethoxylated with 25 oxyethylene units (Hüls).
23. Radiasurf ™ 7417: Stearic acid esterified with polyethylene glycol with a molecular weight of 1500 (Oleofina).
24. Berol ™ 533: C11-alkylalcohol ethoxylated with 3 oxyethylene units (Berol Nobel).
25. Hydropar 19: Paraffinic mineral oil, 19 mPa x s ved 40° C. (Norsk Hydro).
26. Radia 7131: 2-ethylhexylstearate, tecn. (Oleofina).
27. PEG E 200: Polyethylene glycol with a molecular weight of app. 200.
28. Moussex 904 SE: 30% silicone emulsion (Protex).
29. Genamin ™ S 25: Stearyl amine ethoxylated with 25 oxyethylene units (Hoechst).
30. Genapol OX-130: $C_{12-15}$-alkylalcohol ethoxylated with 13 oxyethylene units (Hoechst).

What is claimed is:

1. A concentrated herbicide suspension composition comprising:

5–58% by weight of at least one herbicide, said herbicide being in particulate form suspended in a liquid aqueous phase and comprising at least one amino group, at least one carboxylic acid group and at least one phosphor containing acid group, and at least 5% by weight of an electrolyte, which is dissolved in the liquid, aqueous phase and which is not a surfactant, and 1–5% by weight of one or more surfactants being emulsified, suspended and/or dissolved in the liquid, aqueous electrolyte solution.

2. A composition according to claim 1, having a water content of not more than 65% by weight.

3. A composition according to claim 1, wherein the liquid, aqueous phase is continuous as regards water, contains water miscible organic solvent, and the water content is at least 52% by weight of the total amount of solvent in the liquid phase.

4. A composition according to claim 3, wherein the water content is at least 60% by weight of the total amount of solvent in the liquid phase.

5. A composition according to claim 1, wherein the herbicide is glyphosate, glufosinate, bilanafos and/or glyphosine.

6. A composition according to claim 1, wherein the herbicide is in its non-neutralized form, or is completely or partly converted into its acid or base neutralized salt.

7. A composition according to claim 1, wherein the herbicide is glyphosate, glufosinate, bilanafos and/or glyphosine in its free, non-neutralized form or completely or partly converted into its respective ammonium salt by reaction with ammonia.

8. A composition according to claim 1, wherein the herbicide comprises 10–51% by weight.

9. A composition according to claim 1, wherein the electrolyte is selected from among ammonium salts.

10. A composition according to claim 1, wherein the electrolyte is a member selected from the group consisting of a sulphate, a chloride, a phosphate, a phosphite, a nitrate, a nitrite, a rhodanide, a sulfamate, a sulfite, a dithionite and a thiosulphate.

11. A composition according to claim 1, wherein the amount of dissolved electrolyte is 5–60% by weight.

12. A composition according to claim 1, further comprising 0.1–18% by weight of one or more viscosity regulating compounds.

13. A composition according to claim 12, wherein each viscosity regulating compound has a particle size of up to 5 $\mu$m and is a member selected from the group consisting of a naturally occurring clay, a synthetic clay and a silicate.

14. A composition according to claim 12, wherein the synthetic clay and silicate are selected from the group consisting of a naturally occurring silicium dioxide, a calcium silicate, a magnesium silicate, a magnesium aluminum silicate and an aluminum silicate.

15. A composition according to claim 1, wherein the herbicide has an average particle size of up to 72 $\mu$m.

16. A composition according to claim 1, wherein the herbicide has an average particle size of up to 48 $\mu$m.

17. A composition according to claim 1, wherein the herbicide has an average particle size of 0.5–29 $\mu$m.

18. A composition according to claim 1, having 3 to 38% by weight of surfactant.

19. A composition according to claim 1, comprising at least one surfactant selected from the group consisting of a non-ionic surfactant.

20. A composition according to claim 19, wherein the non-ionic surfactant is ethoxylated, propoxylated or co-ethoxylated/-propoxylated.

21. A composition according to claim 19, wherein the non-ionic surfactant is a member selected from the group consisting of an alkylglycoside, an alkylpolyglycoside, an alkoxylated alkylglycoside, an alkoxylated alkylpolyglycoside, an alkoxylated saccharide, an alkoxylated polysaccharide, an alkoxylated acetylene diol containing a symmetrically substituted triple bond or an ethoxylated polymethylsiloxyane.

22. A composition according to claim 1, which comprises a cationic surfactant selected from the group consisting of $C_{8-30}$-hydrocarbylamine and -diamine and -triamine being alkoxylated with at least 1 oxyethylene and/or oxypropylene group, a quaternary amine with at least one $C_{8-30}$-hydrocarbyl and/or hydrocarbylene group and an alkoxylated derivative thereof, and an amine modified polymethylsiloxane.

23. A composition according to claim 1, which comprises an anionic surfactant selected from the group consisting of a phosphate ester, a sulfonic acid, an ester and halfester of sulfosuccinic acid, a monosulfate ester of $C_{8-20}$-hydrocarbylalcohol and a sterylalcohol derivative, a naphthalene sulfonic acid derivative, a sulfonated vegetable oil and a sulfonated mono- and diester of a natural fatty acid, a tauride and a sarkoside and a sulfamido carbonic acid and an anionic derivative of a polymethylsiloxane.

24. Process for producing a herbicide composition according to claim 1, which comprises the following steps:
(a) producing a concentrated herbicide solution comprising a herbicide in the form of a salt and water,
(b) adding to said concentrated herbicide solution an acid or a base thereby resulting in precipitation of the herbicide in its completely or partly free acid form and formation of an electrolyte solution, which solution comprises the salt initially formed with the herbicide and the acid or base added.

25. An activating additive (adjuvant) in concentrated form for admixture with compositions containing glyphosate- and/or glufosinate for combating weeds, said additive comprising at least one surfactant in an amount of 4–58% by weight being emulsified, suspended and/or dissolved in a liquid, aqueous phase, and at least one undissolved, fine-grained, not biologically active, viscosity regulating filler, said filler acting to prevent the separation of the surfactant and being present in an amount of at least 0.3% by weight, characterized by comprising an electrolyte, which is dissolved in the liquid, aqueous phase and, which is not a surfactant, in an amount of at least 5% by weight.

* * * * *